United States Patent [19]

Grunwell et al.

[11] 4,139,617
[45] Feb. 13, 1979

[54] 19-OXYGENATED-ANDROST-5-ENES FOR THE ENHANCEMENT OF LIBIDO

[75] Inventors: Joyce F. Grunwell, Hamilton, Ohio; Vladimir Petrow, Chapel Hill, N.C.

[73] Assignee: Richardson-Merrell Inc., Wilton, Conn.

[21] Appl. No.: 766,613

[22] Filed: Feb. 7, 1977

Related U.S. Application Data

[63] Continuation-in-part of Ser. No. 469,477, May 13, 1974.

[51] Int. Cl.$^2$ .................. A61K 31/56; A61K 31/58
[52] U.S. Cl. ........................ 424/238; 260/239.55 R; 260/397.3; 260/397.4; 260/397.5; 424/241; 424/242; 424/243
[58] Field of Search ............... 424/238, 241, 242, 243

[56] References Cited

U.S. PATENT DOCUMENTS

| | | | |
|---|---|---|---|
| 3,102,127 | 8/1963 | Bowers | 260/397.4 |
| 3,284,448 | 11/1966 | Cross | 260/239.55 |
| 3,309,387 | 3/1967 | Furst | 260/397.5 |

OTHER PUBLICATIONS

Knox et al, J. Org. Chem. 30, 2198–2205 (1965).
Applezweig, Steroid Drugs (1962), p. 273, Mc Graw–Hill Book Co., Inc., RM 799A6C.5.

*Primary Examiner*—Ethel G. Love
*Attorney, Agent, or Firm*—William J. Stein; Eugene O. Retter; George W. Rauchfuss, Jr.

[57] ABSTRACT

The present invention concerns derivatives of 19-oxygenated-androst-5-enes which are useful in the enhancement of libido and related psychic attitudes.

4 Claims, No Drawings

19-OXYGENATED-ANDROST-5-ENES FOR THE ENHANCEMENT OF LIBIDO

CROSS REFERENCE TO RELATED INVENTION

This application is a continuation-in-part of U.S. application Ser. No. 469,477, filed May 13, 1974.

SUMMARY OF THE INVENTION

This invention relates to the unexpected and surprising discovery that certain novel compounds, in addition to certain compounds previously described in the prior art, possess the property of enhancing a diminished libido in mammals without evoking any overt androgenic or estrogenic response upon the secondary sex structures. More particularly, the class of compounds which possess this novel utility is represented by the formula:

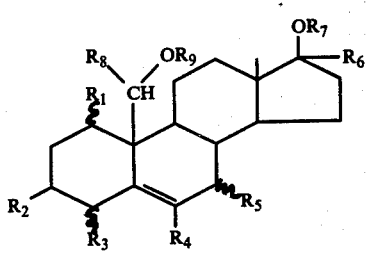

wherein
$R_1$, $R_3$, $R_4$ and $R_5$ are hydrogen and methyl;
$R_2$ is selected from the group consisting of $H_2$, oxo and $H(OR_{10})$;
$R_6$ is selected from the group consisting of hydrogen, lower alkyl having from 1 to 6 carbon atoms, lower alkenyl having from 2 to 6 carbon atoms, lower alkynyl having from 2 to 6 carbon atoms and when taken together with $OR_7$ is oxo;
$R_7$, $R_9$ and $R_{10}$ are each selected from the group consisting of hydrogen, acyl having from 1 to 12 carbon atoms, an ether radical selected from the group consisting of lower alkyl having from 1 to 3 carbon atoms, trialkylsilyl in which the alkyl group has from 1 to 5 carbon atoms, triphenylsilyl, 2-tetrahydropyranyl, 4-tetrahydropyranyl, 1-cycloalkenyl having from 5 to 7 carbon atoms, 1-methoxycycloalkyl and 1-ethoxycycloalkyl in which the cycloalkyl group has from 5 to 7 carbon atoms; and
$R_8$ is hydrogen and when taken together with $OR_8$ is oxo.

DESCRIPTION OF THE PRIOR ART

U.S. Pat. Nos. 3,067,198 and 3,077,482 represent the closest art known to applicants. Disclosed in U.S. Pat. No. 3,067,198 is a class of closely related 19-oxygenated-$\Delta^5$-3-hydroxy-steroids. U.S. Pat. No. 3,077,482 discloses a corresponding class of closely related 19-oxygenated-$\Delta^5$-3-oxo-steroids. Both these classes of compounds have been expressly excluded as new compounds from the novel compounds described herein. The sole utility stated for these prior art references is as a chemical intermediate for the preparation of certain 19-nor-steroids, as for example, 19-nortestosterone and 19-nor-progesterone.

U.S. Pat. No. 3,449,381 discloses similar compounds and additionally discloses the 19-(2'-tetrahydropyranyl)ether thereof. The 19-oxo-androstane compounds and the 19-lower alkyl derivatives thereof are stated to exhibit anabolicandrogenic activity, inhibit the production of pituitary gonadotropic hormones and A.C.T.H. In addition, they are stated to have anti-estrogenic properties, lower blood, liver and adrenal cholesterol levels and to be useful in the control of fertility, psychotic conditions and as appetite stimulants.

U.S. Pat. No. 3,318,923, Column 6, line 8, discloses the compound 7α-methyl-$\Delta^5$-androstene-3β,17β,19-triol as a starting material for the preparation of the corresponding $\Delta^{5(10)}$-6-ol-3-one and its 6-acylate derivative. Although this disclosure represents a non-enabling disclosure without any indication of utility, this compound has, nevertheless, been expressly excluded from the scope of the novel compounds of the present invention.

Mills et al., Chemistry and Industry 946, (1961) disclose the preparation of 6-methylandrost-5-ene-3β,17β,19-triol and its triacetate. No statement of utility is provided, however. These compounds have also been expressly excluded from the novel compounds described herein.

Hormones are generally recognized as being of significance in the biochemical regulation of the psyche and sexual behavior, Hubble, Lancet, August 3, 1963, 209-214. No references are known to applicants, however, which teach or even remotely suggest the unexpected properties that the novel compounds of this invention possess, namely, their unexpected and remarkable ability to enhance the sexual interest and drive of mammals. Furthermore, these compounds can be administered without obtaining any overt, concomitant, androgenic, somatic side effects.

DETAILED DESCRIPTION OF THE INVENTION

As shown in formula (I) above, the compounds of the present invention are androst-5-en-19-ols, ethers or acylates and androst-5-en-19-ones which can be substituted in the 1, 3, 4, 6, 7 and 17-positions of the steroid nucleus.

The symbols $R_1$, $R_3$, $R_4$ and $R_5$ represent either hydrogen or methyl. Thus, the 1, 4, 6 and 7-positions of the androst-5-ene nucleus can remain either unsubstituted, as when these various symbols represent hydrogen, or they may be individually substituted with a methyl group.

The symbol $R_2$ represents various substituents located at the 3-position of the androst-5-ene nucleus. Suitable substituents include two hydrogen atoms, an oxo group, and either a substituted or an unsubstituted hydroxyl group. The substituted or unsubstituted hydroxyl group, represented by the symbol $OR_{10}$, can be present in either its alpha or beta configuration. When the symbol $R_{10}$ represents hydrogen, the free alcohol is, of course, delineated. When the symbol $R_{10}$ represents acyl, an acyl ester derived from a monobasic alkyl or aralkyl carboxylic acid having from 1 to 12 carbon atoms is present at the 3-position. The carboxylic acids from which these acylates are derived include saturated and unsaturated aliphatic acids as well as aromatic acids, as for example, acetic, propionic, butyric, isobutyric, valeric, isovaleric, caproic, caprylic, decanoic, dodecanoic, acrylic, crotonic, cyclobutanecarboxylic, cyclopentanecarboxylic, cyclopentenecarboxylic, cyclohexanecarboxylic, benzoic, toluic, naphthoic, ethylbenzoic, phenylacetic, naphthaleneacetic, phenylvaleric, cinnamic, phenylpropionic, p-propyloxyphenylpropionic and p-butyloxyphenylacetic acid. Finally, the 3-ethers are delineated when the symbol $R_{10}$ represents an ether radical selected from the group consisting of lower alkyl having from 1 to 3 carbon atoms, trialkylsilyl in which the alkyl group has from 1 to 5 carbon atoms, triphenylsilyl, 2-tetrahydropyranyl, 4-tetrahydropyranyl, 1-cycloalkenyl having from 5 to 7 carbon atoms, 1-methoxycycloalkyl and 1-ethoxycycloalkyl in which the cycloalkyl group has from 5 to 7 carbon atoms.

The symbol $R_6$ represents the 17α-position and can be either a hydrogen atom or a saturated or unsaturated aliphatic chain having from 1 to 6 carbon atoms. Illustrative of such groups are straight or branched chain alkyl radicals, as for example, methyl, ethyl, propyl, isopropyl, butyl, sec-butyl, isoamyl, n-pentyl and n-hexyl. Illustrative of the alkenyl groups which can be present are the vinyl, allyl, 1butenyl, 1-pentenyl, and 1-hexenyl radicals. Illustrative of the alkynyl groups which can be present are the ethynyl, 1-propynyl and 1-butynyl radicals. It should be noted that the symbols $R_6$ and $OR_7$ when taken together can also represent an oxo radical, thereby forming a class of substituted androst-5-en-17-ones.

The symbol $OR_7$ represents various oxygenated substituents located at the 17β-position of the steroid nucleus. Suitable substituents include the hydroxyl group, an acyl ester and various lower alkyl, silyl, tetrahydropyranyl and various saturated or unsaturated cycloalkyl ethers. When $R_7$ represents hydrogen, the 17β-hydroxyl group is present. When $R_7$ represents acyl, a carboxylic acyl ester similar to those specifically enumerated for the 3-position is present. The class of 17β-ethers which are present belong to the same class of ethers previously enumerated for the 3-position.

The symbols $R_8$ and $R_9$ delineate the type of oxygenated function present at the 19-position. Thus, when $R_8$ and $R_9$ are both hydrogen the class of androst-5-en-19-ols is defined. The symbol $R_9$ also represents an acyl group having from 1 to 12 carbon atoms thereby describing a class of esters similar to those specifically enumerated for the 3-position, as for example, androst-5-en-19-ol acylates. The class of 19-ethers is circumscribed when the symbol $R_9$ represents an ether radical as previously described for the 3 and 17β-positions. These ethers include the class of lower alkyl, silyl, tetrahydropyranyl and saturated or unsaturated cycloalkyl ethers. The class of androst-5-en-19-ones is defined when the symbols $R_8$ and $OR_9$ are taken together to form the oxo group.

A preferred group of compounds included within the scope of the present invention is the class of 3β-alcohols, esters and ethers of androst-5-en-19-ol. These compounds are delineated where the symbol $R_2$, representing the 3-position, is H($OR_{10}$) and $R_{10}$ is hydrogen, acyl having from 1 to 12 carbon atoms, an ether radical selected from the group consisting of lower alkyl having from 1 to 3 carbon atoms, trialkylsilyl in which the alkyl group has from 1 to 5 carbon atoms, triphenylsilyl, 2-tetrahydropyranyl, 4-tetrahydropyranyl, 1-cycloalkenyl having from 5 to 7 carbon atoms, 1-methoxycycloalkyl and 1-ethoxycycloalkyl in which the cycloalkyl group has from 5 to 7 carbon atoms. Additionally, the symbols $R_8$ and $R_9$ must both be hydrogen in order to define the 19-hydroxy group.

Illustrative species which are encompassed within the preferred group of compounds include 3β-hydroxy-17α-methylandrost-5-ene-17β,19-diol, 1α-methyl-17β-(2'-tetrahydropyranyloxy)-3β-triphenylsiloxyandrost-5-en-19-ol, 3β,17β-di(1'-cyclopentenyloxy)-17α-vinylandrost-5-en-19-ol, 17α-ethyl-3β-(1'-methoxycyclopentyloxy)-4α-methylandrost-5-ene-17β,19-diol 17-acetate, 6-methyl-17β-propoxyandrost-5-ene-3β,19-diol, 3β,19-dihydroxy-7α-methylandrost-5-en-17-one 3-acetate, 1α,4α-dimethyl-3β,19-dihydroxy-androst-5-en-17-one-3-acetate, 3β-(1'-cycloheptenyloxy)androst-5-ene-17β,19-diol 17-propionate, 17α-(1'-ethynyl)-3β,17β-diisopropoxy-7α-methylandrost-5-en-19-ol, 17β-(1'-ethoxycycloheptyloxy)-17α-ethyl-4α,7α-dimethylandrost-5-ene-3β,19-diol 3-acetate, 3β-ethoxy-19-hydroxy-androst-5-en-17-one, 1β,6-dimethyl-androst-5-ene-3β,17β,19-triol, 17β-ethoxy-17α-hexyl-3β-tributylsiloxyandrost-5-en-19-ol, 3β,19-dihydroxy-7α-methylandrost-5-en-17-one, 17α-butyl-3β-(1'-methoxycyclohexyloxy)-1α,7α-dimethylandrost-5-ene-17β,19-diol 17-decanoate, 4α,6-dimethyl-17α-(1'-propynyl)-3β,17β-di(4'-tetrahydropyranyloxy)androst-5-en-19-ol, 3β,19-dihydroxy-androst-5-en-17-one 3-propionate and 1α,4α,7α-trimethyl-3β-trimethylsiloxyandrost-5-ene-17β,19-diol.

Another preferred group of compounds included within the scope of the present invention is the class of 3β-ethers of androst-5-en-19-ones. These compounds are delineated where the symbol $R_2$, representing the 3-position, is H($OR_{10}$) and $R_{10}$ is hydrogen, acyl having from 1 to 12 carbon atoms or an ether radical selected from the same group of ether radicals previously described for the 3-position. Additionally, the symbols $R_8$ and $OR_9$ when taken together are oxo.

Illustrative species which are encompassed within this preferred group of compounds include 17β-hydroxy-17α-methyl-3β-(trimethylsiloxy)androst-5-en-19-one, 3β-hydroxy-1β-methyl-17β-(2'-tetrahydropyranyloxy)androst-5-en-19-one, 3β,17β-di(4'-tetrahydropyranyloxy)-17α-vinylandrost-5-en-19-one, 17α-ethyl-3β,17β-dihydroxy-4α-methylandrost-5-en-19-one 17-acetate, 3β-(1'-cyclohexenyloxy)-6-methyl-17β-propoxyandrost-5-en-19-one, 7α-methyl-3β-(tributylsiloxy)androst-5-ene-17,19-dione, 1α,4α-dimethyl-3β-hydroxy-androst-5-ene-17,19-dione 3-propionate, 3β-hydroxy-17β-hydroxyandrost-5-en-19-one, 3β-hydroxy-17α-(ethynyl)-17β-hydroxy-7α-methylandrost-5-en-19-one 3-acetate, 17α-ethyl-3β,17β-diisopropoxy-4α,7α-dimethylandrost-5-en-19-one, 3β-hydroxyandrost-5-ene-17,19-dione 3-acetate, 1α,6-dimethyl-3β,17β-di(4'-tetrahydropyranyloxy)androst-5-en-19-one, 17α-hexyl-3β,17β-di(trimethylsiloxy)androst-5-en-19-one, 7α-methyl-3β-propoxyandrost-5-ene-17,19-dione, 17α-butyl-3β,17β-dihydroxy-1α,7α-dimethylandrost-5-en-19-one 17β-decanoate, 3β,17β-di(1'-cyclopentenyloxy)-4α,6-dimethyl-17α-(1'-propenyl)androst-5-en-19-one, 3β-triphenylsiloxyandrost-5-ene-17,19-dione, and 3β,17β-dihydroxy-1β,4α,7α-trimethylandrost-5-en-19-one.

The novel alkyl ethers are prepared from their corresponding hydroxy steroids by reaction with an alkylating agent such as trimethyloxonium fluoroborate, triethyloxonium fluoroborate or methylfluorosulfonate in an inert chlorocarbon solvent such as methylene chloride. Alternatively, alkylating agents such as alkyl halides, alkyl tosylates, alkyl mesylates and dialkylsulfate may be used with a base such as silver oxide or barium oxide in polar, aprotic solvents as for example, dimethylformamide, dimethyl sulfoxide and hexamethylphosphoramide. The hydroxyl groups can be silylated by reaction with silylating agents such as trialkylchlorosilane, triarylchlorosilane, N-trialkylsilylacetamide in the presence of an amine base such as triethylamine or pyridine to prepare the novel silyl ethers.

The 2-tetrahydropyranyl ethers are prepared from the corresponding hydroxy steroids by reaction with dihydropyran in the presence of an acid catalyst, as for example, hydrochloric acid, p-toluenesulfonic acid or phosphorous oxychloride.

The 4-tetrahydropyranyl ethers are prepared by reacting the hydroxy steroid, 4-bromotetrahydropyran and a base such as sodium hydride together in a polar aprotic solvent such as dimethylformamide, dimethylsulfoxide or hexamethylphosphoramide.

The 1-alkoxycycloalkoxy derivatives are prepared by reacting the hydroxy steroids with a loweralkylketal of a cycloalkanone or the lower alkylenol ether of a cycloalkanone or mixture of these reagents in the presence of an acidic catalyst such as p-toluenesulfonic acid, pyridine hydrochloride, pyridine p-toluenesulfonate. The reaction is generally conducted in a solvent such as dioxane, methylene chloride, ether or t-butanol at a temperature less than 70° C., and preferably at 25° C. The preparation of suitable cycloalkyl derivatives is achieved using such reagents as cyclopentanone diethylketal, cyclohexanone dimethylketal, 1-methoxy-1-cyclopentene or 1-ethoxy-1-cyclohexene. Following essentially the same procedure, the 1-cycloalkenyl ethers are prepared directly using, however, higher boiling solvents so that the reaction temperature is above 70° C. Suitable solvents include benzene, toluene and dimethylformamide. Alternatively, the 1-cycloalkenylethers can be prepared via a pyrolysis of the isolated 1-alkoxycycloalkoxysteroid in the presence of a trace of an organic base such as pyridine utilizing a high boiling solvent such as benzene or dimethylformamide.

Acyl groups are introduced by standard methods such as the reaction of a hydroxysteroid with an acid anhydride or acid chloride in the presence of a base such as pyridine.

Reduction of 19-hydroxy-5-androstene-3-one with metal hydrides such as lithium aluminum hydride or lithium tri-t-butoxyaluminum hydride produces the 5-androstene-3β,19-diol. The use of a highly hindered lithium or potassium trialkylborohydride such as potassium tri-sec-butylborohydride results in the formation of the 3α-alcohols, namely the 5-androstene-3α,19-diols. Sodium or potassium borohydride reductions of the enol esters of 19-substituted 4-androsten-3-ones furnishes 19-substituted 5-androsten-3-ols.

The 19-aldehyde is prepared from the corresponding 19-alcohol utilizing one of two procedures. A Jones oxidation utilizing exactly one equivalent of reagent and conducted in the cold, preferably between −20° and 10° C., yields the aldehyde without overoxidation to the acid. Alternatively, the Pfitzner-Moffatt procedure with dimethylsulfoxide, dicyclohexylcarbodiimide, pyridine and trifluoroacetic acid in benzene at room temperature produces the 19-aldehyde from the 19-alcohol.

The 3-deoxy-5-androstene analogues are prepared from the 19-substituted-5-androsten-3β-ols. Reaction with thionyl chloride forms the 3β-chloro-19-substituted-5-androstene which is then reductively cleaved to form the 19-substituted-5-androstene by lithium and liquid ammonia.

The 19-substituted-5-androsten-3-ones used as both synthetic intermediates and as final products of the present invention are available from either the 19-substituted-5-androsten-3β-ols or the 19-substituted-4-androsten-3-ones. Both the Jones oxidation and the Pfitzner-Moffatt oxidation procedures which were discussed above will oxidize the 19-substituted-5-androsten-3β-ols to the corresponding 19-substituted-5-androsten-3-ones without double bond migration.

The 19-substituted-4-androsten-3-ones are readily deconjugated to the 19-substituted-5-androsten-3-ones by reaction with a strong base such as sodium methoxide, potassium t-butoxide or lithium isopropylamide in aprotic polar solvents such as dimethylsulfoxide, dimethylformamide or hexamethylphosphoramide to form the enolate anion. Protonation of this enolate anion with weak acids such as ammonium chloride or acetic acid allows the isolation of the corresponding 19-substituted-5-androsten-3-ones in good yields. Care must be taken during the acid quench to work rapidly and to maintain all solutions below 10°–15° C.

The 1,4,6 and 7-methyl-19-substituted-5-androstenes of the present invention can be prepared by introduction of the methyl groups into a 19-substituted androstene as follows. The reaction of dichlorodicyanobenzoquinone with 19-hydroxy-4-androsten-3-ones in refluxing dioxane or methylenechloride for 24–72 hours produces the corresponding 19-hydroxy-1,4-androstadien-3-one. However, two restrictions in this reaction sequence are necessary. First, the 19-hydroxy group must be protected as an ester or ether in order to avoid aromatization. Secondly, the 1-position must possess an axial hydrogen atom for elimination. Thus, the 1α-methyl androstene is not reactive whereas the 1β-methyl androstane is reactive. Following this procedure 17β,19-di(trimethylsiloxy)-4-androsten-3-one is converted to 17β,19-di(trimethylsiloxy)-1,4-androstadien-3-one. Similarly, 19-hydroxy-6α-methyl-4-androsten-3,17-dione acetate forms 19-hydroxy-6α-methyl-1,4-androstadien-3,17-dione acetate and 1β-methyl-19-tetrahydropyranyloxy-4-androsten-3,17-dione forms 1-methyl-19-tetrahydropyranyloxy-1,4-androstadien-3,17-dione.

The 1α-methyl-19-substituted-androst-4-en-3-ones are produced by reacting the corresponding androsta-1,4-dien-3-ones with dimethyllithium copper. Methylation is preferably conducted by adding the androsta-1,4-dien-3-one dissolved in an inert solvent to a solution of dimethyllithium copper in the same or in a different inert solvent. Suitable inert reaction solvents include methylene chloride, tetrahydrofuran, dioxane, hexane, benzene with diethyl ether being the preferred solvent. The reaction is conducted at temperatures between −75° C. and 20° C. with a temperature range of from about −5° C. to 0° C. preferred. The ratio of reactants is not critical, but at least 2 molar equivalents of dimethyllithium copper must be present for each conjugate addition. The presence of free hydroxyl groups will, of course, require additional equivalent amounts of the organometallic reagent. Quenching the initially formed enolate anion with either a strong protonating agent such as hydrochloric acid or a weak protonating agent such as ammonium chloride provides the 1α-methyl-19-substituted-4-androsten-3-one. Following this procedure, 19-hydroxy-androst-1,4-diene-3,17-dione propionate can be converted to 19-hydroxy-1α-methylandrost-4-en-3,17-dione propionate. Deconjugation by reaction with potassium t-butoxide in dimethylsulfoxide followed by an aqueous ammonium chloride quench yields 19-hydroxy-1α-methyl-5-androstene-3,17-dione. Alternatively, the 19-substituted-1,4-androstadien-3-one can be deconjugated to the corresponding 19-substituted-1,5-androstadien-3-one which is reacted with dimethyllithium copper. By limiting the acid quench of the enolate anion to weak protonating agents such as ammonium chloride, the 1α-methyl-19-substituted-5-androsten-3-one is isolated. Following this procedure 17β,19-di(trimethylsiloxy)-1,4-androstadien-3-one is converted to 17β,19-di(trimethylsiloxy)-1,5-androstadien-3-one and then to 1α-methyl-17β,19-di(trimethylsiloxy)-5-androsten-3-one.

The 1β-methyl-19-substituted-4-androsten-3-ones are synthesized in the manner of Simmons and Smith by treatment of a 19-substituted-androsta-1,5-diene-3β-ol with methylenediiodide and a zinc-copper couple to form the 19-substituted-1β,2β-methylene-androst-5-ene-3β-ol. The presence of the 3β-alcohol as well as the 19-alcohol direct the insertion to the beta isomer. The 1β,2β-methylene-3β-ol is oxidized to a 3-one and the cyclopropyl ring cleaved by acid or base to form the 19-substituted-1β-methyl-4-androsten-3-one. Typically a mixture of zinc-copper couple, iodine and methylenediiodide in an inert solvent such as diethylether, tetrahydrofuran, dioxane or diglyme is heated with an infrared lamp for thirty minutes. The steroid, also in an inert solvent as above, is added and the mixture heated from 25° C. to 100° C. for 30 minutes to 72 hours. Generally, reflux temperatures of the solvent employed combined with a 24 hour reflux period is sufficient. The Simmons-Smith reagent is taken in 5-10 fold excess. The oxidation of the 3-alcohol is readily achieved with various oxidizing agents. Illustrative oxidizing agents are Jones reagent, $CrO_3$.pyridine complex (Sarett reagent), and Cornforth reagent. However, if the 19-alcohol is not suitably protected, it will also be oxidized. The remaining 1β,2β-methylene ring is cleaved to the 1β-methyl group by refluxing with zinc in acetic acid. In this manner 19-tetrahydropyranyloxy-1,5-androstadien-3,17-diol is converted to 19-hydroxy-1β-methyl-4-androstene-3,17-dione. Deconjugation via routes described above provides the 19-hydroxy-1β-methyl-5-androstene-3,17-dione.

Methylation of 19-hydroxy-4-androsten-3-ones using Atwater's procedure (N. W. Atwater, J. Am. Chem. Soc. 79, 5315 (1957)) of adding methylchloride slowly to a refluxing solution of the ketone in t-butanol containing only a small excess of potassium t-butoxide produces the 19-hydroxy-4-methyl-4-androsten-3-ones in fair yield. Subsequent deconjugation furnishes the corresponding 5-enes. Following these procedures 19-hydroxy-7α-methyl-androst-4-ene-3,17-dione and 17β,19-hydroxy-1α,7α-dimethyl-androst-4-en-3-one are converted to 19-hydroxy-4,7α-dimethyl-androst-5-ene-3,17-dione and 17β,19-dihydroxy-1α,4,7α-trimethyl-androst-5-en-3-one, respectively. Alternatively, the 19-hydroxy-4-androsten-3-one can be selectively thiomethylated at the 4-position with formaldehyde and a thiol under basic conditions. Benzylmercaptan is the preferred thiol. Desulphurisation of the intermediate 19-hydroxy-4-phenylthiomethyl-4-androsten-3-one leads to the monomethylated 19-hydroxy-4-methyl-4-androsten-3-one in good yield. Subsequent deconjugation furnishes the corresponding 5-enes.

Treatment of a 5α,6α-epoxyandrostane-3,19-diol or a 3,3-ethylenedioxy-5α,6α-epoxyandrostan-19-ol with methylmagnesium bromide in a dry solvent such as diethyl ether, tetrahydrofuran, benzene or toluene at temperatures between 0° C. to 100° C., results in epoxide cleavage to form the corresponding 6β-methylandrostane-5α,19-diols. The corresponding 3-alcohol can be oxidized or the ketal group hydrolysed with hot acetic acid or dilute aqueous methanolic mineral acid to form the 5α-hydroxy-6β-methyl-3-ketone. Dehydration of the β-hydroxy ketone with sodium hydroxide in hot aqueous methanol is accompanied by inversion at 6 to form the 6α-methylandrost-4-en-3-one. Deconjugation yields the 6-methyl-5-androsten-3-ones. In this manner the compounds 17β,19-dihydroxy-6-methyl-5-androsten-3-one, 17β-hydroxy-6,17α-dimethyl-5-androstene-3,19-dione are prepared starting with 3,3-ethylenedioxy-5α,6α-epoxyandrostan-17,19-diol and 5α,6α-epoxy-17α-methylandrostan-3β,17β,19-diol, respectively.

The 7α-methyl-5-androstene-3,19-diones are produced by alkylating the corresponding 4,6-androstadiene-3,19-diones with dimethyllithium copper in an inert solvent such as diethyl ether, tetrahydrofuran, hexane or mixtures thereof at temperatures ranging from −78° C. to 25° C. Tetrahydrofuran is the preferred solvent and temperatures between −5° C. to 10° C. provide optimum results. Quenching the initially formed enolate anion with a weak protonating agent such as a saturated solution of ammonium chloride, oxalic acid or boric acid provides the 7α-methyl-5-androstene-3,19-diones. Following this procedure 1α,7α-dimethyl-5-androstene-3,17,19-trione, 7α-methyl-17β-(2'-tetrahydropyranyloxy)-5-androstene-3,19-dione and 17β-hydroxy-7α,17α-dimethyl-5-androstene-3,19-dione are prepared starting with 1α-methyl-4,6-androstadiene-3,17,19-trione, 17β-(2'-tetrahydropyranyloxy)-4,6-androstadiene-3,19-dione and 17β-hydroxy-4,6-androstadiene-3,19-dione, respectively. Quenching the enolate with a strong protonating agent such as hydrochloric acid provides the 7α-methyl-4-androstene-3,19-diones.

The 7α-methyl-4-androstene-3,19-dione can also be prepared by either acid or base catalyzed isomerization of the corresponding 7α-methyl-5-androstene-3,19-dione. Suitable acid catalysts include hydrochloric acid, sulfuric acid, p-toluenesulfonic acid and acetic acid and these catalysts can be used in such solvents as methanol, ethanol, dioxane, tetrahydrofuran and methylenechloride. Suitable base catalysts for this isomerization include sodium hydroxide or sodium methoxide in an alcohol solvent such as methanol. These 7α-methyl-4-androstene-3,19-diones can be reduced to the diols with reagents such as lithium aluminum hydride, lithium tri-t-butoxyaluminumhydride, sodium borohydride or potassium borohydride. The 3-hydroxyl group can then be selectively oxidized with reagents specific for allylic alcohol oxidation such as activated manganese dioxide or dichlorodicyanobenzoquinone. Following this procedure 19-hydroxy-4-androsten-3-one can be prepared, additionally, 1α,7α-dimethyl-4-androstene-3,17,19-trione can be converted to 1α,7α-dimethyl-4-androstene-3β,17β,19-triol and 17β,19-dihydroxy-1α,7α-dimethyl-4-androsten-3-one. Similarly, 7α-methyl-17β-(2'-tetrahydropyranyloxy)-4-androstene-3,19-dione can be converted to 7α-methyl-17β-(2'-tetrahydropyranyloxy)-4-androstene-3β,19-diol and 19-hydroxy-7α-methyl-17β-(2'-(tetrahydropyranyloxy)-4-androsten-3-one.

Both the 19-hydroxy-5-androsten-3β-ols and the 19-hydroxy-4-androsten-3-ones used as intermediates in the present invention are prepared by the methods described in Vol. II of Organic Reactions in Steroid Chemistry, Edited by J. Fried and J. A. Edwards, p. 237–87; van Nostrand Reinhold Company, N.Y., (1972). One route to these compounds proceeds from the 5α- halogen-6β,19-ether intermediates. These compounds are prepared from the corresponding 5,6-unsaturated steroids by the addition of a hypohalous acid forming the 5α-halogen-6β-carbinols, which are subsequently cyclized by means of lead tetraacetate or by decomposition of the 6β-hypohalites to yield the desired 5α-halogen-6β,19-ethers. Thus, for example, 3β,17β-dihydroxy-5-androstene diacetate is converted to 5α-bromo-3β,6β,17β-trihydroxyandrostane 3,17-diacetate by means of N-bromoacetamide and perchloric acid. Lead tetraacetate or hypoiodide converts this compound to 5α-bromo-3β,17β-dihydroxy-6β,19-oxidoandrostane 3,17-diacetate. In a similar fashion 3β-hydroxyandrost-5-en-17-one acetate is converted to 5α-bromo-3β,6β-dihydroxyandrostan-17-one 3-acetate, and a lead tetraacetate or hypoiodite oxidation converts this latter compound into 5α-bromo-3β-hydroxy-6β,19-oxidoandrostane-17-one acetate. This 17-ketone can subsequently be reacted with an organometallic reagent such as methylmagnesium bromide or lithium acetylide to form the desired 17α-alkylated 17β-hydroxy derivative.

The 3-oxo-4-ene function can be introduced by oxidizing the 3β-hydroxy-5α-halo-6β,19-oxido intermediate by means of an oxidizing reagent such as chromium trioxide. Subsequent dehydrohalogenation using pyridine or sodium acetate in methanol results in the formation of the corresponding 6β,19-oxidoandrost-4-en-3-one. This 6β,19-ether is reductively cleaved using reagents such as zinc and isopropanol or ethanol, zinc and acetic acid or lithium and ammonia to form the desired 19-hydroxyandrost-4-en-3-one. Cleavage with zinc in acetic acid furnishes the 19-acetate while the use of zinc in alcohol furnishes the free 19-alcohol. Alternatively, the 3β-acetoxy-5α-bromo-6β,19-oxido androstane intermediate can be converted to the 5-androstene-3β,19-diol 3-acetate or 3,19-diacetate by the action of zinc in alcohol or acetic acid. Cleavage with zinc and acetic acid furnishes the 3,19-diacetate while zinc and alcohol furnishes the 3-acetate. This selectivity is useful in preparing 19-derivatives in the presence of the 3-acetate. In addition to providing the 19-hydroxyandrostane starting materials for the introduction of methyl groups at positions 1,4,6 and 7, either singly or in combination, this reaction sequence can also be conducted with the methyl groups already present in these positions to produce the compounds of this invention directly.

An alternative route to the 19-hydroxyandrost-4-en-3-ones proceeds from the 6β,19-oxido-3α,5α-cycloandrostanes used as intermediates. These compounds are prepared, in turn, by a lead tetraacetate or hypoiodite oxidation upon the corresponding 6β-hydroxy-3α,5α-cycloandrostane, an i-steroid. Heating the 6β,19-ether in a solvent such as dimethylsulfoxide with benzoylperoxide results in cleavage and the formation of 19-hydroxyandrost-4-en-3-one directly. Alternatively, the 6β,19 ether can be cleaved to the corresponding 3β,19-dihydroxy-5-androstene using sulfuric acid in an aqueous acetone solution. This latter compound is then oxidized to the desired 19-hydroxyandrost-4-en-3-one by means of an Oppenauer oxidation.

The mixed alcohols, esters, ethers, aldehydes and ketones of the present invention are prepared by means of selective oxidation, reduction, protection and hydrolysis sequences on the intermediate androst-4-enes and the androst-5-enes. Thus, a 5-androstene-3β,19-diol diester can be selectively hydrolyzed to the 19-monoester by a one to two hour reflux in 10% aqueous methanol containing one equivalent of potassium bicarbonate. In this manner, for example, 3β,19-dihydroxy-5-androsten-17-one dipropionate can be hydrolyzed to 3β,19-dihydroxy-5-androsten-17-one 19-propionate.

A 5-androstene-3β,17β,19-triol triester can be selectively hydrolyzed to the 17-monoester by the action of potassium carbonate in aqueous methanol at room temperature for about two hours. In addition, a 17β,19-dihydroxy-4-androsten-3-one diester can be selectively hydrolyzed to the 17-monoester by refluxing one hour in 10% aqueous methanol containing one equivalent of sodium bicarbonate. In this manner, for example, 17β,19-dihydroxy-4-methyl-4-androsten-3-one dipropionate and 17β,19-dihydroxy-4-androsten-3-one diacetate are converted to 17β,19-dihydroxy-4-methyl-4-androsten-3-one 17-propionate and 17β,19-dihydroxy-4-androsten-3-one 17-acetate, respectively.

A 19-hydroxy-4-androstene-3,17-dione can be selectively reduced to 17β,19-dihydroxy-4-androsten-3-one by the action of potassium borohydride in ethanol at −10° to 0° C. for reaction periods of less than 5 hours. In this manner 6α-methyl-19-(2'-tetrahydropyranyloxy)-4-androsten-3,17-dione and 19-ethoxy-1α-methyl-4-androstene-3,17-dione can be selectively reduced to 17β-hydroxy-6α-methyl-19-(2'-tetrahydropyranyloxy)-4-androsten-3-one and 19-ethoxy-17β-hydroxy-1α-methyl-4-androsten-3-one, respectively.

A 4-androstene-3β,17β,19-triol can be selectively oxidized to a 17β,19-dihydroxy-4-androsten-3-one using activated manganese dioxide in an inert solvent such as methylene chloride or chloroform at temperatures below 5° C. Elevated temperatures promote oxidation at the 19-position. This selective allylic oxidation is also accomplished by the action of dichlorodicyanobenzoquinone on the triol in solvents such as dioxane or methylenechloride. Preferably the temperature is kept below 25° C. and typical reaction times range from 1 to 18 hours. Using these reagents 1β-methyl-4-androstene-3β,17β,19-triol and 17α-ethinyl-4-androstene-3β,17β,19-triol are converted to 17β,19-dihydroxy-1β-methyl-4-androsten-3-one and 17β-ethinyl-17β,19-dihydroxy-4-androsten-3-one, respectively.

The reductive cleavage of the acetates of 5α-bromo-6β,19-oxidoandrostan-3β-ols by means of zinc in ethanol yields the corresponding 5-androstene-3β,19-diols 3-acetate. In contrast thereto, the action of zinc in acetic acid on the acetates of 5β-bromo-6β,19-oxidoandrostan-3β-ols furnishes the 5-androstene-3β,19-diols diacetates. Selective potassium bicarbonate hydrolysis of these diacetates, as described above, results in the formation of the corresponding 5-androstene-3β,19-diols 19-acetate. Thus, zinc and acetic acid cleavage of 5α-bromo-3β-hydroxy-6β,19-oxidoandrostan-17-one provides 3β,19-dihydroxy-5-androsten-17-one diacetate. A subsequent lithium tri-t-butoxyaluminum hydride reduction results in the formation of 5-androstene-3β,17β,19-triol 3,19-diacetate. The 17β-hydroxy group can now be converted to an ether such as 17β-methoxy-5-androstene-3β,19-diol diacetate or 17β-(4'-tetrahydropyranyloxy)-5-androstene-3β,19-diol diacetate. A controlled bicarbonate hydrolysis as previously described cleaves the 3-acetate to provide the corresponding 19-monoacetate, as for example, the compounds 17β-methoxy-5-androstene-3β,19-diol 19-acetate and 17β-(4'-tetrahydropyranyloxy)-5-androstene-3β,17β-diol 19-acetate which are subsequently illustrated. Oxidation with Jones Reagent or the Pfitzner-Moffatt procedure provides the corresponding 5-en-3-ones. Esterification or etherification of the 3-hydroxyl group provides the corresponding mixed ether/esters.

19-Hydroxy-4-androstene-3,17-diones can be etherified in the manner previously described to prepare the 19-ether-4-androstene-3,17-diones. These compounds can be deconjugated to prepare the corresponding 19-ether-5-androstene-3,17-diones. Lithium aluminum hydride or lithium trialkoxyaluminum hydride reduction results in the preparation of the corresponding 19-ether-5-androstene-3$\beta$,17$\beta$-diols. In this manner, for example, 19-trimethylsiloxyandrost-4-ene-3,17-dione, 19-tetrahydropyranyloxyandrost-4-ene-3,17-dione and 19-methoxyandrost-4-ene-3,17-dione are converted to 19-trimethylsiloxyandrost-5-en-3$\beta$,17$\beta$-diol, 19-(4'-tetrahydropyranyloxy)-androst-5-ene-3$\beta$,17$\beta$-diol and 19-methoxyandrost-5-ene-3$\beta$,17$\beta$-diol, respectively.

17$\beta$,19-Dihydroxy-4-androsten-3-ones can be similarly etherified and deconjugated to form the corresponding 17,19-diether-5-androsten-3-ones. Reduction, as previously described, yields the corresponding 3-alcohols. In this manner, 17$\beta$,19-dihydroxy-1$\alpha$,7$\alpha$,17$\alpha$-trimethyl-4-androsten-3-one can be converted to 1$\alpha$,7$\alpha$,17$\alpha$-trimethyl-17$\beta$,19-di(triphenylsiloxy)-5-androsten-3$\beta$-ol.

The following reaction sequences illustrate the preparation of the two preferred classes of libido-enhancing agents, namely the 3-ether-5-androsten-19-ols and the 3-ether-5-androsten-19-ones. 3$\beta$,19-Dihydroxy-5-androsten-17-one 19-acylate type compounds are etherified to form the 3$\beta$-ether-19-hydroxy-5-androsten-17-one acylates. Lithium aluminum hydride reduction provides the corresponding 3-ether-5-androstene-17$\beta$,19-diols, whereas a lithium tri-t-butoxyaluminum hydride reduction provides the corresponding 3-ether-5-androstene-17$\beta$,19-diol 19-acylates. These latter compounds can be etherified to form the 3-ether-17-ether-5-androsten-19-ol acylates which can subsequently be base hydrolyzed to form the free 19-alcohols. The 19-alcohols are then oxidized to the corresponding 19-aldehydes.

In order to prepare the 3-ether-19-hydroxy-5-androsten-17-ones and the corresponding 3-ether-5-androstene-17,19-diones the 3$\beta$-ether-19-hydroxy-5-androsten-17-one acylates are first base hydrolyzed to form the free 19-alcohols which are then oxidized to the corresponding 19-aldehydes.

5-Androstene-3$\beta$,17$\beta$,19-triol triacylate type compounds can be selectively hydrolyzed as previously described using potassium bicarbonate to form the corresponding 17,19-diacylates. The 3-hydroxyl group is then etherified and the 19-acylate selectively hydrolyzed as described above using potassium carbonate to form the corresponding 3-ether-5-androstene-17$\beta$,19-diol 17-acylates. A Jones oxidation followed by base hydrolysis provides the 3-ether-17$\beta$-hydroxy-5-androsten-19-ones. These compounds can be reduced with lithium aluminum hydride, lithium tri-t-butoxyaluminum hydride or sodium borohydride to form the corresponding 3-ether-5-androstene-17$\beta$,19-diols.

The compounds of this invention, as represented by formula (I) above, are useful in modulating the behavior of normal, non-hostile animals when placed in contact with hostile aggressive animals. Hostile aggression in animals can be induced by a prolonged isolation of individual animals in the dark. Modulation of the behavioral response in the treated, normally non-hostile animals towards the aggressive animals broadly suggests their use in humans for certain psychasthenic syndromes and related conditions of mental health.

Applicants have made the further important discovery that the 19-oxygenated-androst-5-enes described in formula (I) above, enhance the libido of mammals. Illustrative of the term mammals are such species as mice, rats, guinea pigs, rabbits, ferrets, dogs, cats, cows, horses and primates including man. The expression "libido" as used herein refers, in general, to the sexual interest and sexual drive of mammals. However, as used herein, the expression "libido" is also intended to include certain psychic attitudes in primates, particularly man, associated with a diminished libido, relating to the mental and emotional well-being of an individual.

The mental well-being of concern herein is reflected in the degree of mental activity, mental awareness, drive and energy of the individual. The emotional well-being of concern herein is exhibited in the creativity, enthusiasm and social awareness of the individual. Individuals whose psychic attitudes are diminished are apt to feel "down" or depressed and morose. Individuals having enhanced psychic attitudes are more alert and perceptive; they are better able to perform routine repetitive mental tasks.

Libido is generally recognized to be the result of a complex interaction of factors in which genetic, anatomic, neurologic, psychologic and biochemical factors all play prominent roles. The exact mechanism by which the compounds of this invention achieve their effect is not understood except to the extent that it is known to be attributable to some form of biochemical mechanism. Secretions of the endocrine glands are known to affect the psyche. Thus, there is a degree of positive correlation between testosterone blood level changes and dominant or aggressive behavior. Testosterone infusion is also known to improve mental performance in repetitive mental tasks. It has recently been suggested that a dysgenesis of androgen steroids may have a bearing in schizophrenia, cf., Alias, A. G., Lancet, 1248-9, No. 2 (1972).

The fact that libido in both men and women bears a relationship to the endocrine system, and more particularly, to the steroidal hormones associated therewith, has been previously reported, and is clinically recognized. Physicians are often confronted with patients having a variety of symptoms including those of a diminished libido and related psychasthenia, which may be either organic or psychosomatic in origin. Heretofore, therapy employing the administration of testosterone and its esters, or the orally active 17-methyltestosterone has frequently been employed. Adjunctive androgen therapy is also recommended for the restoration of libido in women with certain gynecologic disturbances and in women who have had oophorectomy and bilateral adrenalectomy. Similarly, androgen therapy has been used to restore libido in impotent men whose impotence has been associated with an endocrine malfunction or insufficiency, as for example, in Addison's disease, castration, diabetes mellitus, eunuchoidism, feminizing interstitial-cell tumors, infantilism and obesity.

Although in some patients such treatment has been effective, it has generally proven to be disappointing due to the physiological side effects of the androgen which soon become apparent. In the female, therapeutic doses of testosterone can produce a virilizing effect including hirsuitism, hoarseness or deepening of the voice and an increase in uterine weight. In the male such symptoms as an increased growth of body hair, an increase in weight of the ventral prostate, enlarged seminal vesicles, increased seminal fluid and sterility have been observed. In striking contrast to the androgens previously utilized for this purpose, the libido of mammals and the psychic attitudes associated therewith in primates are enhanced without any overt, concomitant, androgenic, somatic side-effects upon the sex accessory structures by the administration of the androst-4-en-19-ones described in formula (I) above.

The castrated rhesus monkey is a useful primate model in which to demonstrate and observe enhanced libidinous behavior. However, the size and temperament of these animals, plus the expense of maintaining large monkey colonies, makes them unsuitable for ordinary routine screening of large numbers of compounds. Whereas the castrated rat is a useful model for the observation of libidinous behavior, the castrated/adrenalectomized rat provides an even higher degree of correlation with primates such as the castrated monkey. The castrated or the castrated-adrenalectomized rat is a more practicable and manageable animal model that can be accommocated in the large numbers required for the successful testing of compounds and are the standard experimental animals employed for the evaluation of chemical compounds by those skilled in the art.

Administration of the 19-oxygenated-androst-5-enes above to castrated or castrated-adrenalectomized rats results in both an increase in the number and frequency of mounts, intromissions and ejaculations as compared with castrated control animals. Notably, there is observed a decrease in the refractory period following emission. This refractory or post-ejaculatory period for the rat refers to the time period following emission and prior to remounting. During this period the male rat is sexually inert and will even resist any sexual advances made by the female. Many observers feel the refractory period provides a more realistic evaluation of libido enhancement. On necropsy examinations of the secondary sex organs of the animals treated, i.e., the ventral prostate and seminal vesicles, fail to show any overt, peripheral, somatic effects normally associated with androgen administration, and more particularly associated with the administration of testosterone.

The compounds of the present invention can be administered in various unit dosage forms including tablets or lozenges for purposes of absorption through the buccal mucosa. The active ingredient may be enclosed in hard or soft gelatin capsules, or it may be compressed directly into tablets, or they may be incorporated with other pharmaceutical excipients and inert diluents and used in the form of troches, elixirs, suspensions, syrups, wafers, chewing gum and the like. Such compositions and preparations can contain anywhere from 0.1 milligram to about 3 grams of active compound per dosage unit form. Preferably an amount of active ingredient ranging from 0.1 milligram to 500 milligrams is employed per dosage unit. The tablets, troches, pills and capsules may also contain the following pharmaceutical excipients: a binder such as gum tragacanth, acacia, corn starch or gelatin; a diluent such as dicalcium phosphate; a disintegrating agent such as corn starch, potato starch, alginic acid; a lubricant such as magnesium stearate; a sweetening agent such as sucrose, lactose or saccharin, and flavoring agents such as peppermint, oil of wintergreen or cherry flavoring. Various other materials may also be present as coatings or to otherwise modify the physical form of the dosage unit, as for example, shellac-coated tablets or capsules and sugar-coated tablets. Syrups or elixirs may contain the active ingredients, sucrose as a sweetening agent, methyl and propyl parabens as preservatives, and a suitable dye or flavoring agent.

Parenteral fluid dosage forms or injectable forms including those which can be administered by a jet gun are prepared by utilizing the active ingredient in a sterile liquid vehicle such as water or saline solution. Compositions having the desired clarity, stability and adaptability for parenteral use are obtained by dissolving from about 0.1 milligram to about 3 grams of the active ingredient in a vehicle consisting of a mixture of non-volatile, liquid polyethylene glycols which are soluble in water and organic liquids and which have molecular weights ranging from about 200 to about 1,500. Such solutions may advantageously contain suspending agents, such as sodium carboxymethylcellulose, methylcellulose, polyvinyl pyrrolidone or polyvinyl alcohol. In the case of injectable forms, they may also contain preservatives in the nature of bactericidal and fungicidal agents, as for example, parabens, benzyl alcohol, phenol or thimerosal. If desired, isotonic agents are included such as various sugars of sodium chloride. Adjuvants include local anesthetics and stabilizing or buffering agents may also be usefully employed.

The active ingredient can also be compressed into pellets or small cylinders and implanted subcutaneously or intramuscularly as depot injections or implants. Implants may employ inert materials such as biodegradable polymers or synthetic silicones, as for example, Silastic, silicone rubber manufactured by the Dow-Corning Corporation. Implantation results in a slow but, nevertheless, predictable rate of absorption from the site of implantation.

The following preparations and examples are illustrative of the preparation of the novel compounds and compositions of the present invention, but are not to be construed as necessarily limiting the scope thereof.

EXAMPLE 1

5α-Bromo-3β,6β-dihydroxyandrostan-17-one-3-acetate

A solution of 3β-hydroxy-5-androsten-17-one acetate in ether is cooled to −5° C. in an ice-methanol bath. A solution of aqueous perchloric acid is added followed by the addition of N-bromoacetamide. Stirring at −5° C. is continued for about two hours followed by the addition of water. The ether layer is separated, washed with water until neutral and concentrated to a small volume at room temperature. The product is filtered and crystallized from an acetone-hexane solution to yield 5α-bromo-3β,6β-dihydroxyandrostan-17-one 3-acetate.

Substituting 5-androstene-3β,17β-diol diacetate and 17α-methyl-5-androstene-3β,17β-diol diacetate for the 3β-hydroxy-5-androsten-17-one acetate above results in the formation of 5α-bromo-androstane-3β,6β,17β-triol 3,17-diacetate and 5α-bromo-17α-methyl-androstane-3β,6β, 17β-triol 3,17-diacetate, respectively.

EXAMPLE 2

5α-Bromo-3β-hydroxy-6β, 19-oxidoandrostan-17-one acetate

A stirred suspension of lead tetraacetate and calcium carbonate in cyclohexane is refluxed for 30 minutes followed by the addition of iodine and 5α-bromo-3β,6β-dihydroxyandrostan-17-one 3-acetate. The stirred mixture is irradiated with a 600 Watt lamp which maintains the mixture at its reflux temperature. After the iodine color has disappeared, the mixture is cooled, filtered and the residue washed with ether. The filtrates are combined and concentrated to 1/5 volume, washed with a 10% sodium thiosulfate solution, washed with water, dried over magnesium sulfate and evaporated under reduced pressure to yield a semi-solid residue. This residue is crystallized from a solution of acetone-hexane to yield 5α-bromo-3β-hydroxy-6β,19-oxidoandrostan-17-one acetate.

Substituting 5α-bromo-androstane-3β,6β,17β-triol 3,17-diacetate and 5α-bromo-17α-methyl-androstane-3β,6β,17β-triol 3,17-diacetate for the 5α-bromo-3β,6β-dihydroxyandrostan-17-one 3-acetate above results in the formation of 5α-bromo-6β,19-oxidoandrostane-3β,17β-diol diacetate and 5α-bromo-17α-methyl-6β,19-oxidoandrostane-3β,17β-diol diacetate, respectively.

EXAMPLE 3

3β,19-Dihydroxy-5-androsten-17-one 3-acetate

Zinc powder is added to a solution of 5α-bromo-3β-hydroxy-6β,19-oxidoandrostan-17-one acetate in ethanol and the mixture heated at its reflux temperature with stirring for about 3 hours. The suspension is filtered and the zinc cake washed with hot ethanol. Removal of the solvent from the combined filtrates affords a residue which when crystallized from an acetone-hexane solution yields 3β,19-dihydroxy-5-androsten-17-one 3-acetate.

Substituting 5α-bromo-6β,19-oxidoandrostane-3β,17β-diol diacetate and 5α-bromo-17α-methyl-6β,19-oxidoandrostane-3β,17β-diol diacetate for the 5α-bromo-3β-hydroxy-6β,19-oxidoandrostan-17-one acetate above, results in the formation of 5-androstene-3β,17β,19-triol 3,17-diacetate and 17α-methyl-5-androstene-3β,17β,19-triol 3,17-diacetate, respectively.

EXAMPLE 4

3β,19-Dihydroxy-5-androsten-17-one diacetate

Zinc powder is added to a solution of 5α-bromo-3β-hydroxy-6β,19-oxidoandrostan-17-one acetate in acetic acid and the mixture heated at its reflux temperature with stirring for about 3 hours. The suspension is filtered and the zinc cake washed with hot acetic acid. The combined filtrates are poured onto ice water with vigorous stirring. The solid which forms is collected by vacuum filtration and washed with water. Crystallization from acetone yields 3β,19-dihydroxy-5-androsten-17-one diacetate.

Substituting 5α-bromo-6β,19-oxidoandrostane-3β,17β-diol diacetate and 5α-bromo-17α-methyl-6β,19-oxidoandrostane-3β,17β-diol diacetate for the 5α-bromo-3β-hydroxy-6β,19-oxidoandrostan-17-one acetate above results in the formation of 5-androstene-3β,17β,19-triol triacetate and 17α-methyl-5-androstene-3β,17β,19-triol triacetate, respectively.

EXAMPLE 5

3β,19-Dihydroxy-5-androsten-17-one

A solution of 3β,19-dihydroxy-5-androsten-17-one 3-acetate and 5% aqueous sodium carbonate in methanol is heated at its reflux temperature for approximately two hours. The solvent is removed under reduced pressure and ether added. The ethereal solution is separated, washed with water, dried over magnesium sulfate and evaporated in vacuo. The residue obtained is crystallized from an acetone-hexane solution to yield 3β,19-dihydroxy-5-androsten-17-one.

Substituting 5-androstene-3β,17β,19-triol triacetate for the 3β,19-dihydroxy-5-androsten-17-one 3-acetate above results in the preparation of 5-androstene-3β,17β,19-triol.

EXAMPLE 6

3β,19-Dihydroxy-5-androsten-17-one 19-acetate

To a solution of 3β,19-dihydroxy-5-androsten-17-one diacetate in methanol is added one equivalent of an aqueous 2% solution of potassium hydrogen carbonate. The resulting mixture is heated at its reflux temperature for approximately 2 hours. The solution is evaporated to a small volume under reduced pressure and ether added. The ethereal solution is separated, washed thoroughly with water, dried over magnesium sulfate and evaporated in vacuo. The residue which remains is dissolved in a minimum volume of benzene and chromatographed on a column of silica gel. The column is eluted with a benzene-ethylacetate solution Evaporation of the eluate results in the preparation of pure 3β,19-dihydroxy-5-androsten-17-one 19-acetate.

Substituting 5-androstene-3β,17β,19-triol triacetate for the 3β,19-dihydroxy-5-androsten-17-one diacetate above results in the preparation of 5-androstene-3β,17β,19-triol 17,19-diacetate.

EXAMPLE 7

5-Androstene-3β,17β,19-triol 17-acetate

A solution of 5-androstene-3β,17β,19-triol triacetate in methanol and potassium carbonate in water is combined and stirred at room temperature for a period of about 2 hours. The solution is poured onto water and the solid which forms is collected by filtration. Crystallization of this solid from an acetone solution yields 5-androstene-3β,17β,19-triol 17-acetate.

Substituting 17α-methyl-5-androstene-3β,17β,19-triol triacetate and 17α-ethinyl-5-androstene-3β,17β,19-triol triacetate for the 5-androstene-3β,17β,19-triol triacetate above results in the formation of 17α-methyl-5-androstene-3β,17β,19-triol 17-acetate and 17α-ethinyl-5-androstene-3β,17β,19-triol 17-acetate, respectively.

EXAMPLE 8

5-Androstene-3β,17β,19-triol 3-acetate

A tetrahydrofuran solution of 3β,19-dihydroxy-5-androsten-17-one 3-acetate is added to a solution of lithium tri-t-butoxyaluminum hydride in tetrahydrofuran. The reaction mixture is stirred overnight at room temperature. Aqueous sodium potassium tartrate is added with stirring until a readily filterable precipitate forms. The filtrate is concentrated under reduced pressure and diluted with ether. The resulting solution is washed with water, dried over magnesium sulfate and concentrated under vacuum. The residue so obtained when crystallized from an acetone-hexane solution furnishes 5-androstene-3β,17β,19-triol 3-acetate.

Substituting 3β,19-dihydroxy-5-androsten-17-one 19-acetate and 3β,19-dihydroxy-5-androsten-17-one diacetate results in the formation of 5-androstene-3β,17β,19-triol 19-acetate and 5androstene-3β,17β,19-triol 3,19-diacetate, respectively.

EXAMPLE 9

5-Androstene-3β,17β,19-triol 19-acetate

To a solution of 5-androstene-3β,17β,19-triol 3,19-diacetate in methanol is added one equivalent of an aqueous 2% solution of potassium bicarbonate. The mixture is heated at its reflux temperature for a period of about 2 hours, concentrated to a small volume under reduced pressure and ether added thereto. The ethereal solution is separated, washed with water, dried over magnesium sulfate and evaporated in vacuo. The residue so obtained is crystallized from an acetone-hexane solution to furnish the desired 5-androstene-3β,17β,19-triol 19-acetate.

EXAMPLE 10

17α-Methyl-5-androstene-3β,17β,19-triol

To a solution of 3β,19-dihydroxy-5-androsten-17-one diacetate in ether is added 10 equivalents of ethereal methyl lithium. The resulting mixture is stirred at room temperature for about 18 hours. The reaction mixture is decomposed with aqueous ammonium chloride, the ether layer separated, washed with water, dried over magnesium sulfate and concentrated under vacuum. Crystallization of the residue from an acetone-hexane solution yields pure 17α-methyl-5-androstene-3β,17β,19-triol.

Following essentially the same procedure but substituting 10 equivalents of vinyl lithium in tetrahydrofuran for the ethereal methyl lithium above, results in the preparation of 17α-vinyl-5-androstene-3β,17β,19-triol.

EXAMPLE 11

17α-Ethinyl-5-androstene-3β,17β,19-triol

Dry acetylene is bubbled through dry ether for 30 minutes with stirring. Potassium t-amylate in t-amyl alcohol and 3β,19-dihydroxy-5-androsten-17-one diacetate in ether are added via dropwise addition. Stirring is continued at room temperature for approximately 5 hours while acetylene is bubbled through the reaction mixture. The reaction mixture is acidified with aqueous ammonium chloride containing a few drops of hydrochloric acid and thoroughly extracted with ether. The combined ether extracts are washed with water, dried over magnesium sulfate and evaporated under reduced pressure. The residue remaining is crystallized from an acetone-hexane solution to yield 17α-ethinyl-5-androstene-3β,17β, 19-triol.

EXAMPLE 12

17β,19-Dihydroxy-1,4-androstadien-3-one dipropionate

17β,19-Dihydroxy-4-androsten-3-one dipropionate and dichlorodicyanobenzoquinone are refluxed in anhydrous dioxane for a period of 48 hours. The mixture is cooled and filtered and the filtrate concentrated under vacuum. Methylenechloride is added and the resulting mixture filtered. The filtrate is washed well with water, dried over sodium sulfate and the solvent removed. Chromatography of the residue on silica gel and elution with methylenechloride provides a solid which is crystallized from an acetone-hexane solution to yield the desired 17β,19-dihydroxy-1,4-androstadien-3-one dipropionate.

Substituting 17β,19-dihydroxy-17α-methyl-4-androsten-3-one dipropionate, 17β,19-dihydroxy-6α-methyl-4-androsten-3-one dipropionate, 19-hydroxy-4-androsten-3,17-dione propionate, 17β,19-dihydroxy-7α-methyl-4-androsten-3-one dipropionate and 19-tetrahydropyranyloxy-4-androsten-3,17-dione for the 17β,19-dihydroxy-4-androsten-3-one dipropionate above results in the formation of 17β,19-dihydroxy-17α-methyl-1,4-androstadien-3-one dipropionate, 17β,19-dihydroxy-6α-methyl-1,4-androstadien-3-one dipropionate, 19-hydroxy-1,4-androstadiene-3,17-dione propionate, 17β,19-dihydroxy-7α-methyl-1,4-androstadien-3-one dipropionate and 19-tetrahydropyranyloxy-1,4-androstadiene-3,17-dione, respectively.

EXAMPLE 13

17β,19-Dihydroxy-1α-methyl-4-androst-en-3-one dipropionate

A solution of lithium dimethylcopper is prepared under nitrogen by the addition of 1.6 M ethereal methyllithium to an ether slurry of cuprous iodide at 0° C. The solution is stirred at 0° C. for 20 minutes and a solution of 17β,19-dihydroxy-1,4-androstadien-3-one dipropionate in anhydrous tetrahydrofuran is added slowly and stirred over a period of one half hour. The mixture is poured onto a saturated aqueous ammonium chloride solution, benzene is added and the resulting mixture filtered through diatomaceous earth. The organic layer is washed with aqueous ammonium chloride, water, dried over magnesium sulfate and evaporated to dryness. The residue is passed through a silica gel column and eluted with benzene. Recrystallization from hexane yields 17β,19-dihydroxy-1α-methyl-4-androsten-3-one dipropionate.

Substituting 17β,19-dihydroxy-17α-methyl-1,4-androstadien-3-one dipropionate, 17β,19-dihydroxy-6α-methyl-1,4-androstadien-3-one dipropionate, 19-hydroxy-1,4-androstadiene-3,17-dione propionate and 17β,19-dihydroxy-7α-methyl-1,4-androstadien-3-one dipropionate for 17β,19-dihydroxy-1,4-androstadien-3-one in the above procedure results in the formation of 17β,19-dihydroxy-1α,17α-dimethyl-4-androsten-3-one dipropionate, 17β,19-dihydroxy-1α,6α-dimethyl-4-androsten-3-one dipropionate, 19-hydroxy-1α-methyl-4-androstene-3,17-dione propionate and 17β,19-dihydroxy-1α,7α-dimethyl-4-androsten-3-one dipropionate, respectively.

EXAMPLE 14

17β,19-Dihydroxy-1α-methyl-4-androsten-3-one

A solution of 17β,19-dihydroxy-1α-methyl-4-androsten-3-one dipropionate in methanol is refluxed for two hours with aqueous sodium carbonate. The solvent is removed and the residue dissolved in chloroform. The chloroform solution is washed well with water, dried over magnesium sulfate and evaporated under vacuum. The residue which remains is crystallized from acetonitrile to yield 17β,19-dihydroxy-1α-methyl-4-androsten-3-one.

Substituting 17β,19-dihydroxy-1α,7α-dimethyl-4-androsten-3-one dipropionate, 17β,19-dihydroxy-1α,6α-dimethyl-4-androsten-3-one dipropionate, 19-hydroxy-1α-methyl-4-androsten-3,17-dione propionate and 17β,19-dihydroxy-1α,7α-dimethyl-4-androsten-3-one dipropionate in the above procedure results in the preparation of 17β,19-dihydroxy-1α,17α-dimethyl-4-androsten-3-one, 17β,19-dihydroxy-1α,6α-dimethyl-4-androsten-3-one, 19-hydroxy-1α-methyl-4-androstene-3,17-dione and 17β,19-dihydroxy-1α,7α-dimethyl-4-androsten-3-one, respectively.

EXAMPLE 15

17β,19-Dihydroxy-1α-methyl-5-androsten-3-one

A solution of 17β,19-dihydroxy-1α-methyl-4-androsten-3-one in dimethylsulfoxide is added to a solution of potassium t-butoxide in dimethylsulfoxide precooled to 20° C. The reaction mixture is stirred under nitrogen for 10 minutes at room temperature and then poured onto ice cold aqueous ammonium chloride solution with vigorous stirring. The precipitate is rapidly filtered under vacuum, washed well with water and air dried. Crystallization of this residue from an acetone-hexane solution furnishes pure 17β,19-dihydroxy-1α-methyl-5-androsten-3-one.

Substituting 17β,19-dihydroxy-1α,17α-dimethyl-4-androsten-3-one, 17β,19-dihydroxy-1α,6α-dimethyl-4-androsten-3-one, 19-hydroxy-1α-methyl-4-androstene-3,17-dione and 17β,19-dihydroxy-1α,7α-dimethyl-4-androsten-3-one for the 17β,19-dihydroxy-1α-methyl-4-androsten-3-one above results in the formation of 17β,19-dihydroxy-1α,17α-dimethyl-5-androsten-3-one, 17β,19-dihydroxy-1α,6-dimethyl-5-androsten-3-one, 19-hydroxy-1α-methyl-5-androstene-3,17-dione and 17β,19-dihydroxy-1α,7α-dimethyl-5-androsten-3-one, respectively.

EXAMPLE 16

1α-Methyl-5-androstene-3β,17β,19-triol

A solution of 17β,19-dihydroxy-1α-methyl-5-androsten-3-one in tetrahydrofuran is added to a suspension of lithium aluminum hydride in tetrahydrofuran. After stirring overnight at room temperature an aqueous solution of sodium potassium tartrate is added until a readily filtered granular precipitate forms. This precipitate is removed by filtration and washed well with ether. The filtrate and ether washings are combined, washed with water, dried over magnesium sulfate and concentrated under vacuum. Crystallization of the residue yields 1α-methyl-5-androstene-3β,17β,19-triol.

Substituting 17β,19-dihydroxy-1α,17α-dimethyl-5-androsten-3-one, 17β,19-dihydroxy-1α,6-dimethyl-5-androsten-3-one, 19-hydroxy-1α-methyl-5-androstene-3,17-dione and 17β,19-dihydroxy-1α,7α-dimethyl-5-androstene-3-one for the 17β,19-dihydroxy-1α-methyl-5-androsten-3-one above results in the preparation of 1α,17α-dimethyl-5-androstene-3β,17β,19-triol, 1α,6-dimethyl-5-androstene-3β,17β,19-triol, 1α-methyl-5-androstene-3β,17β,19-triol and 1α,7α-dimethyl-5-androstene-3β,17β,19-triol, respectively.

EXAMPLE 17

19-Hydroxy-1β,2β-methylene-4-androstene-3,17-dione

To a solution of potassium t-butoxide in dimethylsulfoxide at 25° C. under nitrogen is added 19-tetrahydropyranyloxy-1,4-androstadiene-3,17-dione in dimethylsulfoxide with stirring. After 15 minutes the mixture is poured onto cold aqueous solution of ammonium chloride. The solid which forms is rapidly filtered, washed well with water and dissolved in ether. The ether solution is washed with water, dried over sodium sulfate and evaporated at room temperature to yield 19-tetrahydropyranyloxy-1,5-androstadiene-3,17-dione.

A tetrahydrofuran solution of 19-tetrahydropyranyloxy-1,5-androstadiene-3,17-dione is added under nitrogen to a solution of lithium tri-t-butoxyaluminum hydride in tetrahydrofuran. After stirring overnight at room temperature, an aqueous solution of potassium tartrate is added with stirring to form a readily filterable white solid. The reaction mixture is filtered, the filtrate dried over magnesium sulfate and the solvent removed by evaporation. The residue which remains is crystallized from an acetone solution to yield 19-tetrahydropyranyloxy-1,5-androstadiene-3β,17β-diol.

To a stirred solution of 19-tetrahydropyranyloxy-1,5-androstadiene-3β,17β-diol in a mixture of dry ether and glyme is added zinc-copper couple and methylene iodide. This reaction mixture is refluxed for four hours, cooled to room temperature, diluted with ether and filtered. The ether filtrate is washed with an aqueous sodium chloride solution, washed with water, and dried over anhydrous magnesium sulfate. The ether is removed under reduced pressure and the residue which remains is crystallized from an acetone-hexane solution to yield 1β,2β-methylene-19-tetrahydropyranyloxy-5-androstene-3β,17β-diol.

The 1β,2β-methylene-19-tetrahydropyranyloxy-5-androstene-3β,17β-diol is dissolved in acetone and Jones Reagent added until a persistent yellow-orange color appears. After stirring at room temperature for 10 minutes the mixture is poured onto ice water and the precipitate which forms is collected by filtration. This precipitate is dissolved in a solution of hydrochloric acid in aqueous methanol and stirred for 30 minutes at room temperature. The methanol is removed by evaporation and the residue is triturated with water. The solid which results is filtered and crystallized from an acetone solution to yield 19-hydroxy-1β,2β-methylene-4-androstene-3,17-dione.

EXAMPLE 18

19-Hydroxy-1β-methyl-4-androstene-3,17-dione

19-Hydroxy-1β,2β-methylene-4-androstene-3,17-dione, zinc powder, and acetic acid are heated to their reflux temperature for a period of about 1 hour. Upon cooling of the reaction mixture, benzene is added and the resulting suspension filtered. The filtrate is evaporated to dryness under vacuum and the residue remaining is chromatographed on a silica gel column and eluted with methylenechloride. The eluate is evaporated to dryness and the residue is crystallized from an acetone-hexane solution to yield 19-hydroxy-1β-methyl-4-androstene-3,17-dione.

EXAMPLE 19

1β-Methyl-5-androstene-3β,17β,19-triol

To a solution of potassium t-butoxide in dimethylsulfoxide at 25° C. under nitrogen is added with stirring 19-hydroxy-1β-methyl-4-androstene-3,17-dione in dimethylsulfoxide. After 15 minutes the mixture is poured onto a cold aqueous ammonium chloride solution. The solid is rapidly filtered, washed well with water and dissolved in ether. The ether solution is again washed with water and dried over sodium sulfate. The ether is removed at room temperature to yield 19-hydroxy-1β-methyl-5-androstene-3,17-dione.

A tetrahydrofuran solution of 19-hydroxy-1β-methyl-5-androstene-3,17-dione is added under nitrogen to a solution of lithium tri-t-butoxyaluminum hydride in tetrahydrofuran. After stirring at room temperature for about 18 hours, an aqueous solution of potassium sodium tartrate is added with stirring to form a readily filterable white solid. The reaction mixture is filtered, the filtrate dried over magnesium sulfate, and the solvent removed. The residue which remains is crystallized from an acetone-hexane solution to yield 1β-methyl-5-androstene-3β,17β,19-triol.

EXAMPLE 20

1β-Methyl-5-androstene-3β,17β,19-triol triacetate

1β-Methyl-5-androstene-3β,17β,19-triol is dissolved in acetic anhydride and pyridine and maintained at room temperature for approximately 20 hours. The solvents are removed under vacuum and the residue is recrystallized from a solution of hexane to furnish 1β-methyl-5-androstene-3β,17β,19-triol triacetate.

EXAMPLE 21

17β,19-Dihydroxy-4,6α,17α-trimethyl-4-androsten-3-one

A mixture of 17β,19-dihydroxy-6α,17α-dimethyl-4-androsten-3-one, thiophenol, 40% aqueous formaldehyde, triethylamine and ethanol is heated at its reflux temperature for a period of about 48 hours. The cooled solution is poured into aqueous sodium hydroxide and the product isolated by ether extraction. The ether extract is washed with water and dried over magnesium sulfate. The residue left after evaporation of the ether is triturated with hexene to remove condensation products derived from the thiophenol and formaldehyde. The 17β,19-dihydroxy-6α-methyl-4-phenylthiomethyl-4-androsten-3-one so obtained is desulfurized by dissolving in acetone and adding to a suspension of Raney Nickel in refluxing acetone. The resulting mixture is heated at its reflux temperature while stirring for about 5 hours. The hot solution is filtered and the nickel washed with boiling ethanol and water. The combined filtrates are concentrated under vacuum whereupon the product separates as a solid. Recrystallization from acetone-hexane yields 17β,19-dihydroxy-4,6α,17α-trimethyl-4-androsten-3-one.

Following essentially the same procedure and substituting 17β,19-dihydroxy-4-androsten-3-one, 19-hydroxy-1α-methyl-4-androstene-3,17-dione and 17β,19-dihydroxy-7α-methyl-4-androstene-3-one for the 17β,19-dihydroxy-6α,17α-dimethyl-4-androsten-3-one above results in the preparation of 17β,19-dihydroxy-4-methyl-4-androsten-3-one, 19-hydroxy-1α,4-dimethyl-4-androstene-3,17-dione, and 17β,19-dihydroxy-4,7α-dimethyl-4-androsten-3-one, respectively.

EXAMPLE 22

4,6α,17α-Trimethyl-17β,19-di(2'-tetrahydropyranyloxy)-4-androsten-3-one

Dihydropyran is slowly added to a solution of 17β,19-dihydroxy-4,6α,17α-trimethyl-4-androsten-3-one and p-toluenesulfonic acid in anhydrous dioxane. After standing 25 minutes at room temperature, methanolic ammonia is added until the solution becomes slightly basic. The solvent is removed under reduced pressure and the residual oil taken up in ether. This ether solution is washed with an aqueous sodium bicarbonate solution, dried over sodium sulfate and concentrated. Crystallization of the residue from a solution of pentane yields 4,6α,17α-trimethyl-17β,19-di(2'-tetrahydropyranyloxy)-4-androsten-3-one.

Substituting 17β,19-dihydroxy-4-methyl-4-androsten-3-one, 19-hydroxy-1α,4-dimethyl-4-androstene-3,17-dione and 17β,19-dihydroxy-4,7α-dimethyl-4-androsten-3-one for the 17β,19-dihydroxy-4,6α,17α-trimethyl-4-androsten-3-one above results in the preparation of 4-methyl-17β,19-di(2'-tetrahydropyranyloxy)-4-androsten-3-one, 1α,4-dimethyl-19-(2'-tetrahydropyranyloxy)-4-androstene-3,17-dione and 4,7α-dimethyl-17β,19-di(2'-tetrahydropyranyloxy)-4-androsten-3-one, respectively.

EXAMPLE 23

17β,19-Dihydroxy-4,17α-dimethyl-4-androsten-3-one

A solution of 17β,19-dihydroxy-17α-methyl-4-androsten-3-one in t-butanol is heated to boiling and added to a boiling solution of potassium t-butoxide in t-butanol. Methyl chloride in t-butanol is slowly added. The solution is cooled, acidified with concentrated hydrochloric acid, and diluted with water. The t-butanol is removed under vacuum and the aqueous layer extracted with ethylacetate. The extract is washed with water, dried over magnesium sulfate and evaporated in vacuo. The residue which remains is chromatographed on a silica gel column and eluted with ethylacetate. The eluant is concentrated and the residue is crystallized from acetonitrile to yield 17β,19-dihydroxy-4,17α-dimethyl-4-androsten-3-one.

EXAMPLE 24

17β,19-Dihydroxy-4α,6,17α-trimethyl-5-androsten-3-one

A solution of 17β,19-dihydroxy-4,6α,17α-trimethyl-4-androsten-3-one in dimethylsulfoxide is slowly added with stirring under nitrogen to a solution of sodium methoxide in dimethylsulfoxide at 25° C. After standing for about 15 minutes the mixture is poured onto a cold aqueous ammonium chloride solution. The solid which forms is rapidly filtered, washed well with water and dissolved in ether. The ether solution is washed with water, dried over sodium sulfate and the ether removed at room temperature. The residue is crystallized from an acetone-hexane solution to yield 17β,19-dihydroxy-4α,6,17α-trimethyl-5-androsten-3-one.

Substituting 17β,19-dihydroxy-4-methyl-4-androsten-3-one, 19-hydroxy-1α,4-dimethyl-4-androstene-3,17-dione, 17β,19-dihydroxy-4,7α-dimethyl-4-androsten-3-one, 4-methyl-17β,19-di(2'-tetrahydropyranyloxy)-4-androsten-3-one and 1α,4-dimethyl-19-(2'-tetrahydropyranyloxy)-4-androstene-3,17-dione for the 17β,19-dihydroxy-4,6α,17α-trimethyl-4-androsten-3-one above results in the formation of 17β,19-dihydroxy-4α-methyl-5-androsten-3-one, 19-hydroxy-1α,4α-dimethyl-5-androstene-3,17-dione, 17β,19-dihydroxy-4α,7α-dimethyl-5-androsten-3-one, 4α-methyl-17β,19-di(2'-tetrahydropyranyloxy)-5-androsten-3-one and 1α,4α-dimethyl-19-(2'-tetrahydropyranyloxy)-5-androstene-3,17-dione, respectively.

EXAMPLE 25

4α,6,17α-Trimethyl-5-androstene-3β,17β,19-triol

A tetrahydrofuran solution of 17β,19-dihydroxy-4α,6,17α-trimethyl-5-androsten-3-one is added under nitrogen to a solution of lithium aluminum hydride in tetrahydrofuran. The resulting mixture is heated at its reflux temperature with stirring for about 4 hours. An aqueous solution of potassium sodium tartrate is added to the cooled reaction mixture until a readily filterable white solid is formed. The mixture is filtered, the filtrate dried over magnesium sulfate and the solvent removed. The residue obtained is crystallized from an acetone-hexane solution to yield 4α,6,17α-trimethyl-5-androstene-3β,17β,19-triol.

Substituting 17β,19-dihydroxy-4α-methyl-5-androsten-3-one, 19-hydroxy-1α,4α-dimethyl-5-androstene-3,17-dione, 17β,19-dihydroxy-4α,7α-dimethyl-5-androsten-3-one, 4α-methyl-17β,19-di(2'-tetrahydropyranyloxy)-5-androsten-3-one and 1α,4α-dimethyl-19-(2'-tetrahydropyranyloxy)-5-androstene-3,17-dione for the 17β,19-dihydroxy-4α,6,17α-trimethyl-5-androsten-3-one above results in the formation of 4α-methyl-5-androstene-3β,17β,19-triol, 1α,4α-dimethyl-5-androstene-3β,17β,19-triol, 4α,7α-dimethyl-5-androstene-3β,17β,19-triol, 4α-methyl-17β,19-di(2'-tetrahydropyranyloxy)-5-androsten-3β-ol and 1α,4α-dimethyl-19-(2'-tetrahydroyranyloxy)-5-androstene-3β,17β-diol, respectively.

EXAMPLE 26

5α,6α-Epoxy-17α-methyl-androstane-3β,17β,19-triol 3,19-diacetate

A solution of 17α-methyl-5-androstene-3β,17β,19-triol 3,19-diacetate in chloroform is chilled to 0° C. and treated with m-chloroperbenzoic acid in chloroform which is precooled to 0° C. The mixture is stirred and allowed to warm to room temperature. After a period of about 48 hours, the solution is washed with a 10% sodium sulfite solution, a solution of sodium thiosulfate, a sodium bicarbonate solution and water. The chloroform extract is dried over magnesium sulfate and evaporated in vacuo. The residue so obtained is crystallized from methanol to yield 5α,6α-epoxy-17α-methylandrostane-3β,17β,19-triol 3,19-diacetate.

EXAMPLE 27

6β,17α-Dimethyl-androstane-3β,5α,17β,19-tetrol

Ethereal methylmagnesium bromide is slowly added to a stirred solution of 5α,6α-epoxy-17α-methylandrostane-3β,17β,19-triol 3,19-diacetate in tetrahydrofuran. The solution is heated at its reflux temperature for about 24 hours, cooled and poured onto a saturated aqueous ammonium chloride solution. The mixture is extracted with ethylacetate, washed with brine, dried over magnesium sulfate and the solvent removed under reduced pressure. The residue so obtained is crystallized from ethyl acetate to yield 6β,17α-dimethylandrostane-3β,5α,17β,19-tetrol.

EXAMPLE 28

17β-Hydroxy-6α,17α-dimethyl-4-androstene-3,19-dione

6β,17α-Dimethylandrostane-3β,5α,17β,19-tetrol is dissolved in acetone and Jones reagent added with stirring. After about 15 minutes the reaction mixture is poured onto water. After stirring for another 30 minutes the solid is filtered and dissolved in methanol containing sodium hydroxide. After about 2 hours the methanol is removed at room temperature and the residue triturated with water. Recrystallization of this residue from an acetone-water solution yields 17β-hydroxy-6α,17α-dimethyl-4-androstene-3,19-dione.

EXAMPLE 29

17β,19-Dihydroxy-6α,17α-dimethyl-4-androsten-3-one

6α,17α-Dimethyl-4-androstene-3β,17β,19-triol is dissolved in hot chloroform and cooled to 15° C. Activated manganese dioxide is added at such a rate that the temperature does not rise above 25° C. Stirring is continued at room temperature for about 1 hour. The manganese dioxide is removed by filtration through a bed of diatomaceous earth and the chloroform distilled under vacuum. The residue which remains is crystallized from acetonitrile to yield 17β,19-dihydroxy-6α,17α-dimethyl-4-androsten-3-one.

EXAMPLE 30

17β,19-Dihydroxy-6,17α-dimethyl-5-androsten-3-one

To a solution of potassium t-butoxide in dimethylsulfoxide at 25° C. under nitrogen is added 17β,19-dihydoxy-6α,17α-dimethyl-4-androsten-3-one in dimethylsulfoxide with stirring. After about 15 minutes the mixture is poured onto a cold aqueous ammonium chloride solution. The solid which forms is rapidly filtered, washed well with water and dissolved in ether. The ether solution is washed well with water and dried over sodium sulfate. The ether is removed at room temperature to yield 17β,19-dihydroxy-6,17α-dimethyl-5-androsten-3-one.

Substituting 19-hydroxy-6α-methyl-4-androstene-3,17-dione for the 17β,19-dihydroxy-6α,17α-dimethyl-4-androsten-3-one above results in the formation of 19-hydroxy-6-methyl-5-androstene-3,17-dione.

EXAMPLE 31

19-Acetoxy-5α,6α-epoxy-androstane-3,17-dione bis-ethyleneketal

To a solution of 19-acetoxy-5-androstene-3,17-dione bis-ethyleneketal in methylenechloride which has been precooled to 0° C. is added a methylenechloride solution of m-chloroperbenzoic acid also precooled to 0° C. The mixture is stirred at room temperature for about 24 hours and additional methylenechloride is added. The methylenechloride solution is washed sequentially with solutions of sodium sulfite, sodium thiosulfite, sodium bicarbonate and finally with water. The methylenechloride extract is dried over magnesium sulfate and taken to dryness under reduced pressure. Recrystallization of the residue from methanol yields 19-acetoxy-5α,6α-epoxy-androstane-3,17-dione bisethyleneketal.

EXAMPLE 32

5α,19-Dihydroxy-6β-methylandrostane-3,17-dione bis-ethyleneketal

A solution of 19-acetoxy-5α,6α-epoxyandrostane-3,17-dione bis-ethyleneketal in tetrahydrofuran is added to an ethereal solution of methylmagnesium bromide. The resultant mixture is refluxed for approximately 4 hours, cooled and treated with a saturated aqueous ammonium chloride solution. The organic layer is evaporated, extracted with ethylacetate, washed with brine, dried over magnesium sulfate and concentrated. Crystallization of the residue from a solution of acetone-hexane yields 5α,19-dihydroxy-6β-methylandrostane-3,17-dione bis-ethyleneketal.

EXAMPLE 33

19-Hydroxy-6α-methyl-4-androstene-3,17-dione

A solution of 5α,19-dihydroxy-6β-methylandrostane-3,17-dione bis-ethyleneketal in methanol containing aqueous sulfuric acid is heated to its reflux temperature and the solvent removed by evaporation. Crystallization of the residue from an acetone-hexane solution yields 19-hydroxy-6α-methyl-4-androstene-3,17-dione.

EXAMPLE 34

4,6-Androstadiene-3,17,19-trione

19-Hydroxy-4-androstene-3,17-dione and choranil are dissolved in t-butanol and rapidly brought to its reflux temperature. The t-butanol is removed by distillation at atmospheric pressure at such a rate so that the total reflux and distillation time equals one hour. The dark pasty residue is triturated with hot chloroform and cooled. The solid which remains is removed by filtration and the filtrate successively extracted with water, a 2% sodium hydroxide solution and again with water. The organic layer is dried over magnesium sulfate and the solvent removed under vacuum to yield 19-hydroxy-4,6-androstadiene-3,17-dione. The diene so prepared is dissolved in acetone and chilled in an ice bath. Jones reagent is added over a period of about 10 minutes and stirring continued for an additional 45 minutes. The mixture is poured onto water. The solid which forms is filtered and recrystallized from benzene to yield 4,6-androstadiene-3,17,19-trione.

Following essentially the same procedure and substituting 19-hydroxy-4-methyl-4-androstene-3,17-dione, 17β,19-dihydroxy-17α-methyl-4-androsten-3-one and 17β,19-dihydroxy-17α-propinyl-4-androsten-3-one for the 19-hydroxy-4-androstene-3,17-dione above results in the preparation of 4-methyl-4,6-androstadiene-3,17,19-trione, 17β-hydroxy-17α-methyl-4,6-androstadiene-3,19-dione and 17β-hydroxy-17α-propinyl-4,6-androstadiene-3,19-dione.

EXAMPLE 35

7α-Methyl-5-androstene-3,17,19-trione

A solution of lithium dimethylcopper is prepared under nitrogen by the addition of 1.6 M ethereal methyllithium to a slurry of cuprous iodide in anhydrous ether at 0° C. The solution is stirred at 0° C. for 20 minutes and a solution of 4,6-androstadiene-3,17,19-trione in anhydrous tetrahydrofuran is added over a period of 20 minutes and stirred for an additional 30 minutes. The reaction mixture is poured onto a saturated aqueous ammonium chloride solution, benzene added and the resulting mixture is rapidly filtered through a bed of diatomaceous earth. The organic layer is separated, washed with an aqueous ammonium chloride solution, washed with water, dried over magnesium sulfate and evaporated to dryness. The crude product is dissolved in a minimum volume of methylenechloride and rapidly chromatographed on a short column of silica gel packed in methylenechloride. The eluant is evaporated and the residue is crystallized from an acetone-hexane solution to yield 7α-methyl-5-androstene-3,17,19-trione.

Substituting 4-methyl-4,6-androstadiene-3,17,19-trione, 17β-hydroxy-17α-methyl-4,6-androstadiene-3,19-dione and 17β-hydroxy-17α-propinyl-4,6-androstadiene-3,17,19-dione for the 4,6-androstadiene-3,17,19-trione above results in the formation of 4α,7α-dimethyl-5-androstene-3,17,19-trione, 17β-hydroxy-7α,17α-dimethyl-5-androstene-3,19-dione, and 17β-hydroxy-7α-methyl-17α-propinyl-5-androstene-3,19-dione, respectively.

EXAMPLE 36

7α-Methyl-4-androstene-3β, 17β,19-triol

A solution of lithium dimethylcopper is prepared under nitrogen by the addition of 1.6 M ethereal methylithium to a slurry of cuprous iodide in anhydrous ether at 0° C. The solution is stirred at 0° C. for 20 minutes, a solution of 4,6-androstadiene-3,17,19-trione in anhydrous tetrahydrofuran is added over a period of about 20 minutes and stirring continued for an additional 30 minutes. The mixture is poured onto a saturated aqueous ammonium chloride solution, benzene is added and the resulting mixture is rapidly filtered through a bed of diatomaceous earth. The organic layer is washed with an aqueous ammonium chloride solution, water, dried over magnesium sulfate and evaporated to dryness. The crude product is dissolved in aqueous methanol containing a drop of hydrochloric acid. The solution is stirred at room temperature for about 1 hour and poured onto ice-water. The resulting oil is extracted into methylenechloride, washed with water, dried over magnesium sulfate and the solvent removed. The residue which remains is crystallized from an etherhexane solution to yield 7α-methyl-4-androstene-3,17,19-trione.

The trione so prepared is dissolved in ethanol and sodium borohydride added under nitrogen. Stirring is continued for about 1 hour, and the solution poured onto ice water containing a few drops of acetic acid. The solid which forms is filtered, dried and recrystallized from ethanol to yield 7α-methyl-4-androstene-3β,17β,19-triol.

Substituting 4-methyl-4,6-androstadiene-3,17,19-trione, 17β-hydroxy-17α-methyl-4,6-androstadiene-3,19-dione and 17β-hydroxy-17α-propinyl-4,6-androstadiene-3,19-dione for the 4,6-androstadiene-3,17,19-trione above results in the formation of 4,7α-dimethyl-4-androstene-3β,17β,19-triol, 7α,17α-dimethyl-4-androstene-3β, 17β,19-triol and 7α-methyl-17α-propinyl-4-androstene-3β,17β,19-triol, respectively.

EXAMPLE 37

17β,19-Dihydroxy-7α-methyl-4-androsten-3-one

7α-Methyl-4-androstene-3β,17β,19-triol is dissolved in hot chloroform and cooled to 15° C. Activated manganese dioxide is added at a rate such that the temperature does not rise above 25° C. Stirring is continued at room temperature for about 1 hour, the manganese dioxide is removed by filtration through a bed of diatomaceous earth and the chloroform distilled under vacuum. The residue which remains is crystallized from acetonitrile to yield 17β,19-dihydroxy-7α-methyl-4-androsten-3-one.

Substituting 4,7α-dimethyl-4-androstene-3β,17β,19-triol, 7α,17α-dimethyl-4-androstene-3β,17β,19-triol and 7α-methyl-17α-propinyl-4-androstene-3β,17β,19-triol for the 7α-methyl-4-androstene-3β,17β,19-triol above results in the formation of 17β,19-dihydroxy-4,7α-dimethyl-4-androsten-3-one, 17β,19-dihydroxy-7α,17α-dimethyl-4-androsten-3-one and 17β,19-dihydroxy-7α-methyl-17α-propinyl-4-androsten-3-one, respectively.

EXAMPLE 38

7α-Methyl-17β,19-di(2'-tetrahydropyranyloxy)-4-androsten-3-one

To a stirred solution of 17β,19-dihydroxy-7α-methyl-4-androsten-3-one and p-toluenesulfonic acid in ahydrous dioxane is slowly added the compound 2,3-dihydropyran. After 5 minutes, methanolic ammonia is added until the solution is slightly basic. The volatile solvents are removed under vacuum and the residual oil is dissolved in methylenechloride. The methylenechloride solution is extracted with an aqueous sodium bicarbonate solution, dried over sodium sulfate, and concentrated under vacuum. The residue which remains is crystallized from pentane to yield 7α-methyl-17β,19-di(2'-tetrahydropyranyloxy)-4-androsten-3-one.

EXAMPLE 39

17β,19-Dihydroxy-7α-methyl-5-androsten-3-one

To a solution of potassium t-butoxide in dimethylsulfoxide at 25° C. under nitrogen is added with stirring a solution of 17β,19-dihydroxy-7α-methyl-4-androsten-3-one in dimethylsulfoxide. After standing for 15 minutes, the mixture is poured onto a cold aqueous ammonium chloride solution. The solid which forms is rapidly filtered, washed well with water and dissolved in ether. The ether solution is washed well with water and dried over sodium sulfate. The ether is removed at room temperature to yield 17β,19-dihydroxy-7α-methyl-5-androsten-3-one.

Substituting 17β,19-dihydroxy-4,7α-dimethyl-4-androsten-3-one, 17β,19-dihydroxy-7α,17α-dimethyl-4-androsten-3-one, 17β,19-dihydroxy-7α-methyl-17α-propinyl-4-androsten-3-one and 7α-methyl-17β,19-di(2'-tetrahydropyranyloxy)-4-androsten-3-one for the 17β,19-dihydroxy-7α-methyl-4-androsten-3-one above results in the formation of 17β,19-dihydroxy-4α,7α-dimethyl-5-androsten-3-one, 17β, 19-dihydroxy-7α,17α-dimethyl-5-androsten-3-one, 17β,19-dihydroxy-7α-methyl-17α-propinyl-5-androsten-3-one and 7α-methyl-17β,19-di(2'-tetrahydropyranyloxy)-5-androsten-3-one, respectively.

EXAMPLE 40

17β,19-Dihydroxy-1,4,6-androstatrien-3-one diacetate

17β,19-Dihydroxy-4-androsten-3-one diacetate and chloranil are dissolved in t-butanol which is rapidly brought to its reflux temperature. The t-butanol is removed by distillation at atmospheric pressure at such a rate that the total reflux and distillation time equals 1 hour. The dark residue which remains is triturated with hot chloroform and filtered. The filtrate is extracted with water, a 2% sodium hydroxide solution, again with water, dried over magnesium sulfate and the solvent removed by evaporation to yield 17β,19-dihydroxy-4,6-androstadiene-3-one diacetate. The diene so prepared is refluxed with dichlorodicyanobenzoquinone in anhydrous dioxane for about 48 hours. The mixture is cooled, filtered and the filtrate poured onto a mixture of methylenechloride and water. The organic layer is separated, washed with water, dried well over magnesium sulfate and the solvent removed. The dark residue which remains is chromatographed on a silica gel column and eluted with methylenechloride. The eluate yields the desired 17β,19-dihydroxy-1,4,6-androstatrien-3-one diacetate.

EXAMPLE 41

17β,19-Dihydroxy-1α-methyl-4,6-androstadien-3-one diacetate

A solution of lithium dimethylcopper is prepared under nitrogen by the addition of 1.6 M ethereal methyllithium to an ether slurry of cuprous iodide at 0° C. The solution is stirred at 0° C. for 20 minutes, a solution of 17β,19-dihydroxy-1,4,6-androstatrien-3-one diacetate in anhydrous tetahydrofuran is added over a 20-minute period, and the mixture stirred for an additional 30 minutes. The reaction mixture is poured onto a saturated aqueous ammonium chloride solution, benzene is added and the resulting mixture filtered through a bed of diatomaceous earth. The organic layer is separated and washed with an aqueous ammonium chloride solution, washed with water, dried over magnesium sulfate and evaporated to dryness. The residue remaining is crystallized from a hexane solution to yield 17β,19-dihydroxy-1α-methyl-4,6-androstadien-3-one diacetate.

EXAMPLE 42

17β,19-Dihydroxy-1α,7α-dimethyl-5-androsten-3-one diacetate

A solution of 17β, 19-dihydroxy-1α-methyl-4,6-androstadien-3-one diacetate in anhydrous tetrahydrofuran is slowly added to an ice cold ethereal solution of lithium dimethylcopper prepared as in the preceding Example. Stirring is continued for an additional 30 minutes and the mixture is poured onto a saturated aqueous ammonium chloride solution. Benzene is added and the mixture filtered through a bed of diatomaceous earth. The organic layer is separated, washed with aqueous ammonium chloride, washed with water, dried over magnesium sulfate and evaporated to dryness. The residue is chromatographed on a silica gel column and eluted with benzene. The eluant is evaporated and the residue recrystallized from a hexane solution to yield 17β,19-dihydroxy-1α,7α-dimethyl-5-androsten-3-one diacetate.

EXAMPLE 43

19-Hydroxy-5-androsten-17-one acetate

3β,19-Dihydroxy-5-androsten-17-one 19-acetate is dissolved in ether and thionyl chloride added at room temperature. After two minutes the solvent is removed at 45° C. under vacuum. The residue is dried in a vacuum oven over sodium hydroxide for four days to remove any remaining traces of thionyl chloride. The dried residue is crystallized from an ether-hexane solution to furnish 3β-chloro-19-hydroxy-5-androsten-17-one acetate.

A solution of 3β-chloro-19-hydroxy-5-androsten-17-one acetate in anhydrous tetrahydrofuran is added with stirring to a solution of lithium in liquid ammonia. After approximately two hours of stirring, 95% ethanol is added via dropwise addition. The residue obtained after evaporation of the ammonia is treated with water and ether. The ether extract is washed with water, dried over magnesium sulfate and concentrated under vacuum. The residue which remains is crystallized from an acetone-hexane solution to yield 19-hyroxy-5-androsten-17-one acetate.

Substituting 4α-methyl-17β,19-di(2'-tetrahydropyranyloxy)-5-androsten-3β-ol and 1α,7α-dimethyl-5-androstene-3β,17β,19-triol 17,19-diacetate for the 3β,19-dihydroxy-5-androsten-17-one 19-acetate above results in the formation of 4α-methyl-17β,19-di(2'-tetrahydropyranyloxy)-5-androstene and 1α,7α-dimethyl-5-androstene-17β,19-diol diacetate, respectively.

EXAMPLE 44

3β,17β,19-Tri(trimethylsiloxy)androst-5-ene

Androst-5-ene-3β,17β,19-triol is dissolved in dry pyridine and trimethylsilylacetamide added thereto. The reaction is completed at room temperature within a few minutes. The pyridine is removed under reduced pressure and the residue purified from an acetone-hexane solution to yield the desired 3β,17β,19-tri(trimethylsiloxy)androst-5-ene.

Following essentially the same procedure but substituting 17α-methyl-5-androstene-3β,17β,19-triol 3,17-diacetate, androst-5-ene-3β,17β,19-triol 19-acetate, and 4α-methyl-17β,19-di(2'-tetrahydropyranyloxy)-5-androsten-3β-ol for the androst-5-ene-3β,17β,19-triol above results in the formation of 17α-methyl-3β,17β,19-tri(trimethylsiloxy)androst-5-ene, 3β,17β-di(trimethylsiloxy)-5-androsten-19-ol acetate and 4α-methyl-17β,19-di(2'-tetrahydropyranyloxy)-3β-trimethylsiloxy-5-androstene, respectively.

EXAMPLE 45

17β,19-Di(1'-ethoxy-1'-cyclohexyloxy)androst-4-en-3-one

A suspension of 17β,19-dihydroxyandrost-4-en-3-one in anhydrous dioxane is treated at room temperature with pyridine, p-toluenesulfonate and cyclohexanone ethyl enolether. The steroid dissolves and a new precipitate forms which upon standing overnight is filtered and recrystallized from a methanol-methylene chloride solution to yield the desired 17β,19-di(1'-ethoxy-1'-cyclohexyloxy)androst-4-en-3-one.

Using essentially the same procedure but substituting 17β,19-dihydroxy-1α,7α-dimethyl-4-androsten-3-one and 17β,19-dihydroxy-7α-methyl-4-androsten-3-one for the 17β,19-dihydroxyandrost-4-en-3-one above results in the preparation of 17β,19-di(1'-ethoxy-1'-cyclohexyloxy)-1α,7α-dimethyl-4-androsten-3-one and 17β,19-di(1'-ethoxy-1'-cyclohexyloxy)-7α-methyl-4-androsten-3-one.

EXAMPLE 46

17β,19-Di(1'-cyclohexenyloxy)androst-4-en-3-one

17β,19-Di(1'-ethoxy-1'-cyclohexyloxy)androst-4-en-3-one is dissolved in dimethylformamide containing one drop of pyridine. The solution is heated at 150° C. for 1 hour allowing the alcohol which forms to distill. The solvent is removed under vacuum and the residue recrystallized from methanol to yield the desired 17β,19-di(1'-cyclohexenyloxy)androst-4-en-3-one.

In essentially the same manner substituting 17β,19-di(1'-ethoxy-1'-cyclohexyloxy)-1α,7α-dimethyl-4-androsten-3-one and 17β,19-di(1'-ethoxy-1'-cyclohexyloxy)-7α-methyl-4-androsten-3-one for the 17β,19-di(1'-ethoxy-1'-cyclohexyloxy)androst-4-en-3-one above results in the formation of 17β,19-di(1'-cyclohexenyloxy)-1α,7α-dimethyl-4-androsten-3-one and 17β,19-di(1'-cyclohexenyloxy)-7α-methyl-4-androsten-3-one.

EXAMPLE 47

17β,19-Di(1'-cyclohexenyloxy)androst-5-en-3-one

To a solution of potassium t-butoxide in dimethylsulfoxide at 25° C. under nitrogen is added a solution of 17β,19-di(1'-cyclohexenyloxy)androst-4-en-3-one in dimethylsulfoxide with stirring. After 15 minutes the mixture is poured onto a cold aqueous ammonium chloride solution. The solid is rapidly filtered, washed well with water and dissolved in ether. The ether solution is washed well with water and dried over sodium sulfate. The ether is removed at room temperature to yield 17β,19-di(1'-cyclohexenyloxy)-5-androsten-3-one.

Substituting 17β,19-di(1'-cyclohexenyloxy)-1α,7α-dimethyl-4-androsten-3-one and 17β,19-di(1'-cyclohexenyloxy)-7α-methyl-4-androsten-3-one for the 17β,19-di(1'-cyclohexenyloxy)androst-4-en-3-one above results in the formation of 17β,19-di(1'-cyclohexenyloxy)-1α,7α-dimethyl-5-androsten-3-one and 17β,19-di(1'-cyclohexenyloxy)-7α-methyl-5-androsten-3-one, respectively.

EXAMPLE 48

17β,19-Di(1'-cyclohexenyloxy)androst-5-en-3β-ol

17β,19-Di(1'-cyclohexenyloxy)androst-5-en-3-one is dissolved in anhydrous ether and added to a suspension of lithium aluminum hydride in anhydrous ether. After stirring for a period of 16 hours, water is cautiously added. The resulting mixture is filtered, dried over magnesium sulfate and concentrated in vacuo. The residue is crystallized from methanol to yield the desired 17β,19-di(1'-cyclohexenyloxy)androst-5-en-3β-ol.

In the same manner substituting 17β,19-di(1'-cyclohexenyloxy)-1α,7α-dimethyl-5-androsten-3-one and 17β,19-di(1'-cyclohexenyloxy)-7α-methyl-5-androsten-3-one for the 17β,19-di(1'-cyclohexenyloxy)androst-5-en-3-one above, results in the preparation of 17β,19-di(1'-cyclohexenyloxy)-1α,7α-dimethyl-5-androsten-3β-ol and 17β,19-di(1'-(cyclohexenyloxy)-7α-methyl-5-androsten-3β-ol.

EXAMPLE 49

17α-Propynyl-17β,19-di(trimethylsiloxy)-androst-4-en-3-one

17β,19-Dihydroxy-17α-propynyl-androst-4-en-3-one, trimethylchlorosilane, and pyridine are refluxed in toluene for a period of 18 hours. The resulting suspension is filtered, and the toluene removed under vacuum. The remaining residue is recrystallized from a hexane solution to yield the desired 17α-propynyl-17β,19-di(trimethylsiloxy)androst-4-en-3-one.

Substituting 17β,19-dihydroxy-6α,17α-dimethyl-4-androsten-3-one for the 17β,19-dihydroxy-17α-propynylandrost-4-en-3-one above, results in the preparation of 6α,17α-dimethyl-17β,19-di(trimethylsiloxy)androst-4-en-3-one.

EXAMPLE 50

19-Methoxyandrost-4-ene-3,17-dione

19-Hydroxyandrost-4-ene-3,17-dione is dissolved in methylenechloride and trimethyloxonium fluoroborate added thereto. After stirring at room temperature for a period of two hours, water is added to the reaction mixture, the organic layer is separated, dried over magnesium sulfate and the solvent removed under vacuum. The residue is crystallized from an acetone-hexane solution to yield the desired 19-methoxyandrost-4-ene-3,17-dione.

Using essentially the same procedure but substituting 19-hydroxy-1β-methyl-4-androstene-3,17-dione and 19-hydroxy-6α-methyl-4-androstene-3,17-dione for the 19-hydroxyandrost-4-ene-3,17-dione above, results in the formation of 19-methoxy-1β-methyl-4-androstene-3,17-dione and 19-methoxy-6α-methyl-4-androstene-3,17-dione.

EXAMPLE 51

17α-Propynyl-17β,19-di(trimethylsiloxy)-5-androsten-3-one

To a solution of potassium t-butoxide in dimethylsulfoxide at 25° C. under nitrogen is added a solution of 17α-propynyl-17β,19-di(trimethylsiloxy)androst-4-en-3-one in dimethylsulfoxide with stirring. After an additional 15 minutes the mixture is poured onto a cold aqueous ammonium chloride solution. The solid is rapidly filtered, washed well with water and dissolved in ether. The ether solution is washed well with water and dried over sodium sulfate. The ether is removed at room temperature to yield 17α-propynyl-17β,19-di(-trimethylsiloxy)-5-androsten-3-one.

Substituting 6α,17α-dimethyl-17β,19-di(trimethylsiloxy)-4-androsten-3-one, 19-methoxyandrost-4-ene-3,17-dione, 19-methoxy-1β-methyl-4-androstene-3,17-dione and 19-methoxy-6α-methyl-4-androstene-3,17-dione for the 17α-propynyl-17β,19-di(trimethylsiloxy)androst-4-en-3-one above results in the formation of 6,17α-dimethyl-17β,19-di(trimethylsiloxy)-5-androsten-3-one, 19-methoxyandrost-5-ene-3,17-dione, 19-methoxy-1β-methyl-5-androstene-3,17-dione and 19-methoxy-6-methyl-5-androstene-3,17-dione, respectively.

EXAMPLE 52

17α-Propynyl-17β,19-di(trimethylsiloxy)-5-androsten-3β-ol

An ether solution of 17α-propynyl-17β,19-di(trimethylsiloxy)-5-androsten-3-one is added to a lithium aluminum hydride suspension in ether. After heating at its reflux temperature for one hour, the excess hydride is cautiously decomposed with water. The ether solution is separated, dried over sodium sulfate and concentrated under vacuum. The residue obtained is recrystallized from methanol to yield the desired 17α-propynyl-17β,19-di(trimethylsiloxy)-5-androsten-3β-ol.

Substituting 6α,17α-dimethyl-17β,19-di(trimethylsiloxy)-5-androsten-3-one, 19-methoxyandrost-5-ene-3,17-dione, 19-methoxy-1β-methyl-5-androstene-3,17-dione and 19-methoxy-6-methyl-5-androstene-3,17-dione for the 17α-propynyl-17β,19-di(trimethylsiloxy)-5-androsten-3β-ol above results in the preparation of 6α,17α-dimethyl-17β,19-di(trimethylsiloxy)-5-androsten-3β-ol, 19-methoxyandrost-5-ene-3β,17β-diol, 19-methoxy-1β-methyl-5-androstene-3β,17β-diol and 19-methoxy-6-methyl-5-androsten-3β,17β-diol, respectively.

EXAMPLE 53

19-Methoxyandrost-5-ene-3β,17β-diol diacetate

19-Methoxyandrost-5-ene-3β,17β-diol is dissolved in a mixture of acetic anhydride and pyridine and the solution allowed to stand overnight at room temperature. The solvents are removed under vacuum and the remaining residue crystallized from an acetone-hexane solution to yield 19-methoxyandrost-5-ene-3β,17β-diol diacetate.

Substituting 19-methoxy-1β-methyl-5-androstene-3β,17β-diol and 19-methoxy-6-methyl-5-androstene-3β,17β-diol in lieu of the 19-methoxyandrost-5-ene-3β,17β-diol above results in the preparation of 19-methoxy-1β-methyl-5-androstene-3β,17β-diol diacetate and 19-methoxy-6-methyl-5-androstene-3β,17β-diol diacetate.

EXAMPLE 54

3β,17β-Di(1'-cyclopentenyloxy)-19-19-methoxyandrost-5-ene

To a solution of 19-methoxyandrost-5-ene-3β,17β-diol in anhydrous benzene containing p-toluenesulfonic acid is added cyclopentanone diethylketal. The mixture is heated for a period of one hour permitting distillation of the alcohol which forms. After the addition of pyridine, the benzene is removed under vacuum and the residue which remains is recrystallized from methanol to yield the desired 3β,17β-di(1'-cyclopentenyloxy)-19-methoxyandrost-5-ene.

Using the same procedure and substituting 19-methoxy-1β-methyl-5-androstene-3β,17β-diol and 19-methoxy-6-methyl-5-androstene-3β,17β-diol for the 19-methoxyandrost-5-ene-3β,17β-diol above results in the preparation of 3β,17β-di(1'-cyclopentenyloxy)-19-methoxy-1β-methyl-5-androstene and 3β,17β-di(1'-cyclopentenyloxy)-19-methoxy-6-methyl-5-androstene.

EXAMPLE 55

1α,7α-Dimethyl-androst-5-ene-3β,17β,19-triol 17,19-diacetate

To a solution of lithium tri-t-butoxyaluminum hydride in tetrahydrofuran is added a tetrahydrofuran solution of 17β,19-dihydroxy-1α,7α-dimethyl-5-androsten-3-one diacetate. The resulting mixture is stirred at 20° C. for a period of 18 hours after which is added an aqueous solution of sodium potassium tartrate. The mixture is filtered and concentrated to a small volume under reduced pressure. The concentrate is taken up in ether and washed well with water. The combined ether extracts are dried over magnesium sulfate, filtered and the ether removed under vacuum to yield a residue which when crystallized from a mixture of acetone-hexane results in the preparation of the desired 1α,7α-dimethyl-androst-5-ene-3β,17β,19-triol 17,19-diacetate.

Substituting 19-hydroxy-5-androsten-17-one acetate for the 17β,19-dihydroxy-1α,7α-dimethyl-5-androsten-3-one diacetate above, results in the formation of 5-androstene-17β,19-diol 19-acetate.

EXAMPLE 56

1α,7α-Dimethyl-3β-(2'-tetrahydropyranyloxy)-5-androstene-17β,19-diol diacetate

A solution of 1α,7α-dimethyl-5-androstene-3β,17β,19-triol 17,19-diacetate, p-toluenesulfonic acid and 2,3-dihydropyran are stirred for a period of three hours at room temperature. The solution is diluted with ether, washed with an aqueous sodium carbonate solution, washed well with water, dried over sodium sulfate and evaporated to dryness under reduced pressure. Crystallization of the residue from a mixture of acetone-hexane results in the preparation of the desired 1α,7α-dimethyl-3β-(2'-tetrahydropyranyloxy)-5-androstene-17β,19-diol diacetate.

Substituting 5-androstene-17β,19-diol 19-acetate for the 1α,7α-dimethyl-5-androstene-3β,17β,19-triol 17,19-diacetate above results in the preparation of 17β-(2'-tetrahydropyranyloxy)-5-androsten-19-ol acetate.

EXAMPLE 57

1α,7α-Dimethyl-3β-(2'-tetrahydropyranyloxy)-5-androstene-17β,19-diol

A solution of 1α,7α-dimethyl-3β-(2'-tetrahydropyranyloxy)-5-androstene-17β,19-diol diacetate in methanol is refluxed for a period of two hours with an aqueous solution of sodium carbonate. The solvent is removed by evaporation and the residue so obtained is purified by crystallization from methanol to form the desired 1α,7α-dimethyl-3β-(2'-tetrahydropyranyloxy)-5-androstene-17β,19-diol.

Substituting 17β-(2'-tetrahydropyranyloxy)-5-androsten-19-ol acetate for the 1α,7α-dimethyl-3β-(2'-tetrahydropyranyloxy)-5-androstene-17β,19-diol diacetate above results in the formation of 17β-(2'-tetrahydropyranyloxy)-5-androsten-19-ol.

EXAMPLE 58

19-t-Butyldimethylsiloxy-4-androstene-3,17-dione

19-Hydroxy-4-androstene-3,17-dione, t-butyldimethyl-silylchloride and pyridine are mixed in dry dimethylformamide and heated on a steam bath overnight. The reaction mixture is poured onto water and stirred well for 15 minutes. The resulting solid is filtered and dissolved in methylenechloride, dried over magnesium sulfate and the solvent removed by evaporation. The residue which remains is crystallized from an acetone-hexane solution to yield 19-t-butyldimethylsiloxy-4-androstene-3,17-dione.

Following essentially the same procedure and substituting 19-hydroxy-6α-methyl-4-androstene-3,17-dione and 3β,19-dihydroxy-5-androsten-17-one 19-acetate for the 19-hydroxy-4-androstene-3,17-dione above results in the preparation of 19-t-butyldimethylsiloxy-6α-methyl-4-androstene-3,17-dione and 3-t-butyldimethylsiloxy-19-hydroxy-5-androsten-17-one acetate, respectively.

EXAMPLE 59

19-(4'-Tetrahydropyranyloxy)androst-4-ene-3,17-dione

19-Hydroxy-4-androstene-3,17-dione is dissolved in dimethylformamide and heated to 50° C. 4-Bromotetrahydropyran is added to this solution followed by the addition of sodium hydride. Heating and stirring is continued for a period of four hours, the reaction mixture cooled and poured onto ice water. The resulting oil which forms is extracted with ether and the combined ether extracts are washed with water, dried over magnesium sulfate and concentrated to a cream-colored residue. Crystallization of this residue from a hexane solution yields pure 19-(4'-tetrahydropyranyloxy)androst-4-ene-3,17-dione.

Following essentially the same procedure but substituting 19-hydroxy-1β-methylandrost-4-ene-3,17-dione, 19-hydroxy-6α-methyl-4-androstene-3,17-dione and 3β,19-dihydroxy-5-androsten-17-one 19-acetate for the 19-hydroxy-4-androstene-3,17-dione above, accordingly results in the preparation of 1β-methyl-19-(4'-tetrahydropyranyloxy)androst-4-ene-3,17-dione, 6α-methyl-19-(4'-tetrahydropyranyloxy)androst-4-ene-3,17-dione, and 19-hydroxy-3β-(4'-tetrahydropyranyloxy)-5-androsten-17-one acetate, respectively.

EXAMPLE 60

4-Methyl-17β,19-di(4'-tetrahydropyranyloxy)-4-androsten-3-one

17β,19-Dihydroxy-4-methyl-4-androsten-3-one and 4-bromotetrahydropyran are heated to 50° C. in dimethylformamide. Sodium hydride is slowly added and stirring at 50° C. is continued for a period of about 18 hours. The reaction mixture is poured onto ice water and the water extracted with ether. The combined ether extracts are washed with water, dried over magnesium sulfate and concentrated to dryness. The residue which remains is crystallized from a solution of hexane to yield 4-methyl-17β,19-di(4'-tetrahydropyranyloxy)-4-androsten-3-one.

Following the same procedure and substituting 17β,19-dihydroxy-4-androsten-3-one, 17β,19-dihydroxy-1α-methyl-4-androsten-3-one and 17β,19-dihydroxy-7α-methyl-4-androsten-3-one for the 17β,19-dihydroxy-4-methyl-4-androsten-3-one above, results in the formation of 17β,19-di(4'-tetrahydropyranyloxy)-4-androsten-3-one, 1α-methyl-17β,19-di(4'-tetrahydropyranyloxy)-4-androsten-3-one and 7α-methyl-17β,19-di(4'-tetrahydropyranyloxy)-4-androsten-3-one, respectively.

EXAMPLE 61

19-t-Butyldimethylsiloxy-5-androstene-3,17-dione

To a solution of potassium t-butoxide in dimethylsulfoxide at 25° C. under nitrogen is added a solution of 19-t-butyldimethylsiloxy-4-androstene-3,17-dione in dimethylsulfoxide with stirring. After 15 minutes the mixture is poured onto a cold aqueous ammonium chloride solution. The solid which forms is rapidly filtered, washed well with water and dissolved in ether. The ether solution is washed well with water and dried over sodium sulfate. Evaporation of the ether at room temperature yields 19-t-butyldimethylsiloxy-5-androstene-3,17-dione.

Substituting 19-t-butyldimethylsiloxy-6α-methyl-4-androstene-3,17-dione, 19-(4'-tetrahydropyranyloxy)androst-4-ene-3,17-dione, 4-methyl-17β,19-di(4'-tetrahydropyranyloxy)-4-androsten-3-one and 1β-methyl-19-(4'-tetrahydropyranyloxy)-4-androsten-3,17-dione for the 19-t-butyldimethylsiloxy-4-androstene-3,17-dione above results in the preparation of 19-t-butyldimethylsiloxy-6-methyl-5-androstene-3,17-dione, 19-(4'-tetrahydropyranyloxy)androst-5-ene-3,17-dione, 4α-methyl-17β,19-di(4'-tetrahydropyranyloxy)-5-androsten-3-one and 1β-methyl-19-(4'-tetrahydropyranyloxy)-5-androsten-3,17dione, respectively.

EXAMPLE 62

5-Androstene-3α,17β,19-triol

A 1 M solution of lithium tri-sec-butylborohydride in tetrahydrofuran under nitrogen is cooled in a dry ice-acetone bath to about −78° C. and 17β,19-dihydroxy-5-androsten-3-one in tetrahydrofuran is slowly added. The reaction mixture is stirred for a period of two hours at this temperature, warmed to 0° C. and stirring continued for an additional two hours. The reaction mixture is decomposed by the addition of a 3 N sodium hydroxide solution followed by the addition of a 30% hydrogen peroxide solution. Solid potassium carbonate is added and the tetrahydrofuran solution decanted therefrom. The solid residue is washed with fresh tetrahydrofuran and the combined tetrahydrofuran solutions are dried over anhydrous sodium sulfate, filtered, and evaporated. The residue is crystallized from acetone to yield 5-androstene-3α,17β,19-triol.

Substituting 19-t-butyldimethylsiloxy-5-androstene-3,17-dione, 4α-methyl-17β,19-di(4'-tetrahydropyranyloxy)-5-androsten-3-one and 1β-methyl-19-(4'-tetrahydropyranyloxy)-5-androstene-3,17-dione for the 17β,19-dihydroxy-5-androsten-3-one above results in the preparation of 19-t-butyldimethylsiloxy-5-androstene-3α,17-diol, 4α-methyl-17β,19-di(4'-tetrahydropyranyloxy)-5-androsten-3α-ol and 1β-methyl-19-(4'-tetrahydropyranyloxy)-5-androstene-3α,17β-diol, respectively.

EXAMPLE 63

7α-Methyl-5-androstene-3α,17β,19-triol

An 0.5 M solution of potassium tri-sec-butylborohydride in tetrahydrofuran under nitrogen is cooled to −78° C. in a dry ice-acetone bath. 17β,19-Dihydroxy-7α-methyl-5-androsten-3-one in tetrahydrofuran is slowly added. The reaction mixture is stirred for a period of two hours at this temperature, warmed to 0° C., and stirred for an additional two hours. The reaction mixture is decomposed by the addition of a 3 N sodium hydroxide solution followed by a 30% hydrogen peroxide solution. Solid potassium carbonate is added and the tetrahydrofuran solution decanted. The solid residue is washed with fresh tetrahydrofuran and the combined tetrahydrofuran solutions are dried over anhydrous sodium sulfate, filtered and the filtrate removed by evaporation. The residue is crystallized from acetone to yield 7α-methyl-5-androstene-3α,17β,19-triol.

Substituting 17β,19-dihydroxy-4α,17α-dimethyl-5-androsten-3-one and 19-hydroxy-6-methyl-5-androstene-3,17-dione for the 17β,19-dihydroxy-7α-methyl-5-androsten-3-one above results in the preparation of 4,17α-dimethyl-5-androstene-3α,17β,19-triol and 6-methyl-5-androstene-3α,17β,19-triol, respectively.

EXAMPLE 64

19-(Trimethylsiloxy)-4-androstene-3,17-dione

A mixture of 19-hydroxy-4-androstene-3,17-dione, trimethylchlorosilane and pyridine is refluxed in benzene for a period of 18 hours. The resulting suspension is filtered, the volatiles removed in vacuo and concentrated to a yellow oil. The oil is placed upon a silica gel chromatographic column packed in chloroform and eluted with chloroform. The chloroform eluate is evaporated to dryness in vacuo and the residue is recrystallized twice from hexane to yield the desired 19-(trimethylsiloxy)-4-androstene-3,17-dione.

Following essentially the same procedure but substituting triethylchlorosilane and tripropylchlorosilane for the trimethylchlorosilane above results in the formation of 19-(triethylsiloxy)-4-androstene-3,17-dione and 19-(tripropylsiloxy)-4-androstene-3,17-dione, respectively.

Substituting 19-hydroxy-1β-methyl-4-androstene-3,17-dione, 19-hydroxy-6α-methyl-4-androstene-3,17-dione and 5-androstene-3β,17β,19-triol 17,19-diacetate for the 19-hydroxy-4-androstene-3,17-dione above results in the formation of 1β-methyl-19-trimethylsiloxy-4-androstene-3,17-dione, 6α-methyl-19-trimethylsiloxy-4-androstene-3,17-dione and 3β-trimethylsiloxy-5-androstene-17β,19-diol diacetate, respectively.

EXAMPLE 65

19-(Triphenylsiloxy)-4-androstene-3,17-dione

A solution of 19-hydroxy-4-androstene-3,17-dione, triphenylchlorosilane and pyridine contained in 100 ml of benzene is refluxed for a period of 18 hours. The resulting suspension is filtered and concentrated in vacuo to a yellow oil. The oil is placed on a silica gel chromatographic column packed in chloroform which is further eluted with chloroform. The chloroform eluant is evaporated to dryness in vacuo and the residue is recrystallized from methanol to yield 19-triphenylsiloxy-4-androstene-3,17-dione.

Substituting 19-hydroxy-5-androsten-17-one for the 19-hydroxy-4-androstene-3,17-dione above results in the formation of 19-triphenylsiloxy-5-androsten-17-one.

EXAMPLE 66

19-Trimethylsiloxy-5-androstene-3,17-dione

To a solution of potassium t-butoxide in dimethylsulfoxide at 25° C. under nitrogen is added a solution of 19-trimethylsiloxy-4-androstene-3,17-dione in dimethylsulfoxide with stirring. After 15 minutes the mixture is poured onto a cold aqueous ammonium chloride solution. The solid so obtained is rapidly filtered, washed well with water and dissolved in ether. The ether solution is washed well with water, dried over sodium sulfate and the ether removed at room temperature to yield 19-trimethylsiloxy-5-androstene-3,17-dione.

Substituting 1β-methyl-19-trimethylsiloxy-4-androstene-3,17-dione, 6α-methyl-19-trimethylsiloxy-4-androstene-3,17-dione and 19-triphenylsiloxy-4-androstene-3,17-dione for the 19-trimethylsiloxy-4-androstene-3,17-dione above results in the preparation of 1β-methyl-19-trimethylsiloxy-5-androstene-3,17-dione, 6-methyl-19-trimethylsiloxy-5-androstene-3,17-dione and 19-triphenylsiloxy-5-androstene-3,17-dione, respectively.

EXAMPLE 67

19-Trimethylsiloxy-5-androstene-3β,17β-diol

A tetrahydrofuran solution of 19-trimethylsiloxy-5-androstene-3,17-dione is added to lithium aluminum hydride in tetrahydrofuran and the resultant solution stirred overnight at room temperature. An aqueous solution of sodium potassium tartrate is added with stirring until a readily filterable precipitate forms. The filtrate is concentrated under reduced pressure and diluted with ether. The resulting solution is washed with water, dried over magnesium sulfate, and the ether removed under vacuum. The residual 19-trimethylsiloxy-5-androstene-3β,17β-diol so obtained is recrystallized from an acetone-hexane solution.

Substituting 1β-methyl-19-trimethylsiloxy-5-androstene-3,17-dione, 6-methyl-19-trimethylsiloxy-5-androstene-3,17-dione, 19-triphenylsiloxy-5-androstene-3,17-dione and 19-triphenylsiloxy-5-androsten-17-one for the 19-trimethylsiloxy-5-androstene-3,17-diol above results in the preparation of 1β-methyl-19-trimethylsiloxy-5-androstene-3β,17β-diol, 6-methyl-19-trimethylsiloxy-5-androstene-3β,17β-diol, 19-triphenylsiloxy-5-androstene-3β,17β-diol and 19-triphenylsiloxy-5-androsten-17β-ol, respectively.

EXAMPLE 68

3β,17β-Di(triphenylsiloxy)androst-5-en-19-ol acetate

A solution of androst-5-ene-3β,17β,19-triol 19-acetate, triphenylchlorosilane, pyridine and toluene are refluxed for a period of 24 hours. The resulting solid is filtered and the volatile materials are removed under vacuum. The resultant oil is purified by crystallization from a solution of methanol to yield the desired 3β,17β-di(triphenylsiloxy)androst-5-en-19-ol acetate.

EXAMPLE 69

3β,17β-Di(triphenylsiloxy)androst-5-en-19-ol

To an ether solution of 3β,17β-di(triphenylsiloxy)androst-5-en-19-ol acetate is added a suspension of lithium aluminum hydride in ether. After refluxing for a period of one hour, water is cautiously added, the ether solution is separated, dried over sodium sulfate and evaporated under reduced pressure. The residue when purified from an acetone-hexane mixture results in the preparation of the desired 3β,17β-di(triphenylsiloxy)androst-5-en-19-ol.

EXAMPLE 70

3β-Hydroxy-19-(1'-methoxycyclopentyloxy)-5-androsten-17-one acetate

To a suspension of 3β,19-dihydroxy-5-androsten-17-one 3-acetate in dioxane is added with stirring a mixture of cyclopentanone methylenol ether and pyridine p-toluenesulfonate. The steroid quickly dissolves and a new precipitate forms which, after standing overnight, is collected and recrystallized from a methanol-methylene chloride mixture to yield the desired 3β-hydroxy-19-(1'-methoxycyclopentyloxy)-5-androsten-17-one acetate.

Substituting 17α-methyl-5-androstene-3β,17β,19-triol, 5-androstene-3β,17β,19-triol 3,19-diacetate, and 5-androstene-3β,17β,19-triol 17,19-diacetate for the 3β,19-dihydroxy-5-androsten-17-one 3-acetate above results in the preparation of 3β,17β,19-tri(1'-methoxycyclopentyloxy)-17α-methyl-5-androstene, 17-(1'-methoxycyclopentyloxy)-5-androstene-3β,19-diol diacetate and 3β-(1'-methoxycyclopentyloxy)-5-androstene-17β,19-diol diacetate, respectively.

EXAMPLE 71

19-(1'-Cyclopentenyloxy)-3β-hydroxy-5-androsten-17-one acetate

3β-Hydroxy-19-(1'-methoxycyclopentyloxy)-5-androsten-17-one acetate is dissolved in a dimethylformamide solution containing a drop of pyridine. The solution is refluxed permitting the alcohol which forms to distill. After one hour, the remaining solvent is removed under reduced pressure and the residue so obtained is recrystallized from methanol to yield the desired 19-(1'-cyclopentenyloxy)-3β-hydroxy-5-androsten-17-one acetate.

Substituting 3β,17β,19-tri(1'-methoxycyclopentyloxy)-17α-methyl-5-androstene, 17-(1'-methoxycyclopentyloxy)-5-androstene-3β,19-diol diacetate, and 3β-(1'-methoxycyclopentyloxy)-5-androstene-17β,19-diol diacetate for the 3β-hydroxy-19-(1'-methoxycyclopentyloxy)-5-androsten-17-one acetate above results in the formation of 3β,17β,19-tri(1'-cyclopentenyloxy)-17α-methyl-5-androstene, 17-(1'-cyclopentenyloxy)-5-androstene-3β,19-diol diacetate and 3β-(1'-cyclopentenyloxy)-5-androstene-17β,19-diol diacetate, respectively.

EXAMPLE 72

19-(1'-Cyclopentenyloxy)-5-androstene-3β,17β-diol 19-(1'-Cyclopentenyloxy)-3β-hydroxy-5-androsten-17-one acetate is dissolved in anhydrous ether and added to a suspension of lithium aluminum hydride in anhydrous ether. After refluxing for a period of one hour, water is cautiously added and the mixture filtered. The organic layer is separated and dried over sodium sulfate. The dried solution is filtered, concentrated in vacuo and the residue recrystallized from methanol to yield the desired 19-(1'-cyclopentenyloxy)-5-androstene-3β,17β-diol.

EXAMPLE 73

19-(1'-Cyclopentenyloxy)-5-androstene-3β,17β-diol 3-acetate

A tetrahydrofuran solution of 19-(1'-cyclopentenyloxy)-3β-hydroxy-5-androsten-17-one acetate is added to a mixture of lithium tri-t-butoxyaluminum hydride contained in tetrahydrofuran. After stirring at room temperature overnight, an aqueous solution of potassium sodium tartrate is added with stirring to form a readily filterable white solid. The reaction mixture is filtered and the filtrate dried over magnesium sulfate. The dried solution is filtered and the volatile materials removed in vacuo. The remaining residue is crystallized from an acetone-hexane solution to yield 19-(1'-cyclopentenyloxy)-5-androstene-3β, 17β-diol 3-acetate.

EXAMPLE 74

19-Hydroxy-17β-(1'-methoxycyclohexyloxy)-androst-5-en-3-one acetate

To a suspension of 17β,19-dihydroxyandrost-5-en-3-one 19-acetate in anhydrous dioxane is added cyclohexanone methyl enolether and pyridine p-toluenesulfonate. After standing overnight, the precipitate which forms is collected and crystallized from methanol to give the desired 19-hydroxy-17β-(1'-methoxycyclohexyloxy)androst-5-en-3-one acetate.

Substituting 17β,19-dihydroxy-1β-methylandrost-5-en-3-one 19-acetate and 17β,19-dihydroxy-6-methylandrost-5-en-3-one 19-acetate for the 17β,19-dihydroxyandrost-5-en-3-one 19-acetate above results in the formation of 19-hydroxy-17β-(1'-methoxycyclohexyloxy)-1β-methylandrost-5-en-3-one acetate and 19-hydroxy-17β-(1'-methoxycyclohexyloxy)-6-methylandrost-5-en-3-one acetate.

EXAMPLE 75

17β-(1'-Methoxycyclohexyloxy)-5-androstene-3β,19-diol 19-diol 19-acetate

A tetrahydrofuran solution of 19-hydroxy-17β-(1'-methoxycyclohexyloxy)androst-5-en-3-one acetate is added under nitrogen to a solution of lithium tri-t-butoxyaluminum hydride in tetrahydrofuran. After stirring at room temperature overnight, an aqueous solution of potassium sodium tartrate is added with stirring to form a readily filterable white solid. The reaction mixture is filtered and the filtrate dried over magnesium sulfate and the solvent removed. The residue which remains is recrystallized from acetone to yield 17β-(1'-methoxycyclohexyloxy)-5-androstene-3β,19-diol 19-acetate.

Substituting 19-hydroxy-17β-(1'-methoxycyclohexyloxy)-1β-methylandrost-5-en-3-one acetate and 19-hydroxy-17β-(1'-methoxycyclohexyloxy)-6-methylandrost-5-en-3-one acetate for the 19-hydroxy-17β-(1'-methoxycyclohexyloxy)-androst-5-en-3-one acetate above results in the formation of 17β-(1'-methoxycyclohexyloxy)-1β-methylandrost-5-ene-3β,19-diol, 19-acetate and 17β-(1'-methoxycyclohexyloxy)-6-methylandrost-5-ene-3β,19-diol, 19-acetate, respectively.

EXAMPLE 76

5-Androstene-3,17,19-trione

To a solution of 3β,19-dihydroxy-5-androsten-17-one in acetone at 10° C. is added two equivalents of Jones Reagent with stirring. After an additional 15 minutes the upper acetone layer is decanted and poured onto ice water. The precipitate which forms is filtered, washed with water and dissolved in ether. The ether solution is dried over magnesium sulfate and concentrated under reduced pressure. Crystallization of the residue from an acetone-hexane solution yields 5-androstene-3,17,19-trione.

Substituting 5-androstene-3β,17β,19-triol 3-acetate and 4α,17α-dimethyl-5-androstene-3β,17β,19-triol for the 3β,19-dihydroxy-5-androsten-17-one above results in the preparation of 3β-hydroxy-5-androstene-17,19-dione acetate and 17β-hydroxy-4α,17α-dimethyl-5-androstene-3,19-dione, respectively.

EXAMPLE 77

3β,17β-Dihydroxy-17α-methyl-5-androsten-19-one diacetate

A solution of 17α-methyl-5-androstene-3β,17β,19-triol, 3,17-diacetate in acetone at 10° C. is titrated with one equivalent of Jones Reagent with stirring. After an additional 15 minutes the upper acetone layer is decanted and poured onto ice water with vigorous stirring. The precipitate which forms is removed by filtration, washed well with water, and dissolved in ether. The ether solution is dried over magnesium sulfate and the ether removed under vacuum. The residue which remains is crystallized from an acetone-hexane mixture to yield 3β,17β-dihydroxy-17α-methyl-5-androsten-19-one diacetate.

Substituting 17β,19-dihydroxy-1α,17α-dimethyl-5-androsten-3-one, 19-hydroxy-1α-methyl-5-androstene-3,17-dione, 17β,19-dihydroxy-4α,6,17α-trimethyl-5-androsten-3-one, 17β-(2'-tetrahydropyranyloxy)-5-androsten-19-ol and 3β,17β-di(triphenylsiloxy)-5-androstene-19-ol for the 17α-methyl-5-androstene-3β,17β,19-triol 3,17-diacetate above results in the preparation of 17β-hydroxy-1α,17α-dimethyl-5-androstene-3,19-dione, 1α-methyl-5-androstene-3,17,19-trione, 17β-hydroxy-4α,6,17α-trimethyl-5-androstene-3,19-dione, 17β-(2'-tetrahydropyranyloxy)-5-androsten-19-one and 3β,17β-di(triphenylsiloxy)-5-androsten-19-one, respectively.

EXAMPLE 78

1α,4α-Dimethyl-5-androstene-3,17,19-trione

19-Hydroxy-1α,4α-dimethyl-5-androstene-3,17-dione is added to a mixture containing dimethylsulfoxide, benzene, pyridine, trifluoroacetic acid and N,N-dicyclohexylcarbodiimide and allowed to react for about 12 hours at room temperature. Ethyl acetate is added and the reaction mixture is filtered, extracted with a cold solution of sodium bicarbonate, washed with water, and dried over magnesium sulfate. After evaporation of the volatile solvents at room temperature under reduced pressure, the residue which remains is crystallized from an ether-pentane mixture to yield 1α,4α-dimethyl-5-androstene-3,17,19-trione.

Substituting 1α,7α-dimethyl-3β-(2'-tetrahydropyranyloxy)-5-androstene-17β,19-diol for the 19-hydroxy-1α,4α-dimethyl-5-androstene-3,17-dione above results in the preparation of 1α,7α-dimethyl-3β-(2'-tetrahydropyranyloxy)-5-androstene-17,19-dione.

EXAMPLE 79

19Hydroxy-3β-(2'-tetrahydropyranyloxy)-5-androsten-17-one acetate

To a stirred solution of 3β,19-dihydroxy-5-androsten-17-one 19-acetate and p-toluenesulfonic acid in anhydrous dioxane, dihydropyran is slowly added. After 5 minutes methanolic ammonia is added until the solution is slightly basic. The volatile solvents are removed under vacuum and the residual oil is dissolved in methylenechloride. The methylenechloride solution is extracted with an aqueous sodium bicarbonate solution, dried over sodium sulfate and concentrated under vacuum. The residue which remains is crystallized from a hexane solution to yield 19-hydroxy-3β-(2'-tetrahydropyranyloxy)-5-androsten-17-one acetate.

EXAMPLE 80

3β-(2'-Tetrahydropyranyloxy)-5-androstene-17β,19-diol

To a solution of 19-hydroxy-3β-(2'-tetrahydropyranyloxy)-5-androsten-17-one, acetate in ethanol is added sodium borohydride. The reaction mixture is stirred under nitrogen for a period of about three hours. The solution is poured onto water containing one drop of glacial acetic acid. The precipitate which forms is filtered, washed with water and dried in a vacuum oven. Crystallization of this solid from an ether-pentane mixture yields 3β-(2'-tetrahydropyranyloxy)-5-androstene-17β,19-diol.

Substituting 3-t-butyldimethylsiloxy-19-hydroxy-5-androsten-17-one acetate and 19-hydroxy-3β-(4'-tetrahydropyranyloxy)-5-androsten-17-one acetate for the 19-hydroxy-3β-(2'-tetrahydropyranyloxy)-5-androsten-17-one, acetate above results in the preparation of 3-t-butyldimethylsiloxy-5-androsten-17β,19-diol and 3β-(4'-tetrahydropyranyloxy)-5-androstene-17β,19-diol, respectively.

EXAMPLE 81

19-Hydroxy-3β-(2'-tetrahydropyranyloxy)-5-androsten-17-one

A solution of 19-hydroxy-3β-(2'-tetrahydropyranyloxy)-5-androsten-17-one acetate and sodium carbonate in aqueous methanol is heated to its reflux temperature for a period of about three hours, concentrated to half volume and poured onto water. The oil which forms is extracted into ether. The ether extract is washed with water, dried over magnesium sulfate and the ether removed by evaporation. Crystallization of the residue from an ether-pentane mixture yields 19-hydroxy-3β-(2'-tetrahydropyranyloxy)-5-androsten-17-one.

Substituting 3-t-butyldimethylsiloxy-19;1 -hydroxy-5-androsten-17-one acetate and 19-hydroxy-3β-(4'-tetrahydropyranyloxy)-5-androsten-17-one acetate for the 19-hydroxy-3β-(2'-tetrahydropyranyloxy)-5-androsten-17-one acetate above results in the preparation of 3-t-butyldimethylsiloxy-19-hydroxy-5-androsten-17-one and 19-hydroxy-3β-(4'-tetrahydropyranyloxy)-5-androsten-17-one, respectively.

EXAMPLE 82

3β-(2'-Tetrahydropyranyloxy)-5-androstene-17,19-dione

To a solution of 19-hydroxy-3β-(2'-tetrahydropyranyloxy)-5-androsten-17-one in acetone chilled to 10° C. is added exactly one equivalent of Jones Reagent. After standing for 30 minutes the acetone layer is poured onto water with vigorous stirring. The solid is vacuum filtered, air dried and crystallized from a solution of hexane to provide 3β-(2'-tetrahydropyranyloxy)-5-androstene-17,19-dione.

Substituting 3-t-butyldimethylsiloxy-19-hydroxy-5-androsten-17-one and 19-hydroxy-3β-(4'-tetrahydropyranyloxy)-5-androsten-17-one for the 19-hydroxy-3β-(2'-tetrahydropyranyloxy)-5-androsten-17-one above results in the preparation of 3-t-butyldimethylsiloxy-5-androstene-17,19-dione and 3β-(4'-tetrahydropyranyloxy)-5-androstene-17,19-dione, respectively.

EXAMPLE 83

3β-(2'-Tetrahydropyranyloxy)-5-androstene-17β,19-diol 19-acetate

To a solution of lithium tri-t-butoxyaluminum hydride in tetrahydrofuran is added a tetrahydrofuran solution of 19-hydroxy-3β-(2'-tetrahydropyranyloxy)-5-androsten-17-one acetate. The resulting mixture is stirred at 20° C. for a period of about 18 hours following which an aqueous solution of sodium potassium tartrate is added. The resulting mixture is filtered and concentrated to a small volume under reduced pressure. The concentrate is dissolved in ether and washed well with water. The ether solution is dried over magnesium sulfate, filtered and the ether removed in vacuo to yield a residue. Crystallization of this residue from an acetone-hexane mixture yields 3β-(2'-tetrahydropyranyloxy)-5-androstene-17β,19-diol, 19-acetate.

Substituting 3-t-butyldimethylsiloxy-19-hydroxy-5-androsten-17-one acetate and 19-hydroxy-3β-(4'-tetrahydropyranyloxy)-5-androsten-17-one acetate for the 19-hydroxy-3β-(2'-tetrahydropyranyloxy)-5-androsten-17-one acetate above results in the formation of 3-t-butyldimethylsiloxy-5-androstene-17β,19-diol 19-acetate and 3β-(4'-tetrahydropyranyloxy)-5-androstene-17β,19-diol 19-acetate, respectively.

EXAMPLE 84

3β-(2'-Tetrahydropyranyloxy)-17β-trimethylsiloxy-5-androsten-19-ol acetate

3β-(2'-Tetrahydropyranyloxy)-5-androstene-17β,19-diol 19-acetate is dissolved in dry pyridine and trimethylsilylacetamide added thereto. The reaction is completed at room temperature within a few minutes. The pyridine is removed under reduced pressure and the residue which remains is crystallized from an ether-pentane mixture to yield 3β-(2'-tetrahydropyranyloxy)-17β-trimethylsiloxy-5-androsten-19-ol acetate.

Substituting 3-t-butyldimethylsiloxy-5-androstene-17β,19-diol 19-acetate and 3β-(4'-tetrahydropyranyloxy)-5-androstene-17β,19-diol 19-acetate for the 3β-(2'-tetrahydropyranyloxy)-5-androstene-17β,19-diol 19-acetate above results in the formation of 3-t-butyldimethylsiloxy-17β-trimethylsiloxy-5-androstene-19-ol acetate and 3β-(4'-tetrahydropyranyloxy)-17β-trimethylsiloxy-5-androsten-19-ol acetate, respectively.

EXAMPLE 85

3β-(2'-Tetrahydropyranyloxy)-17β-trimethylsiloxy-5-androsten-19-ol

A solution of 3β-(2'-tetrahydropyranyloxy)-17β-trimethylsiloxy-5-androsten-19-ol acetate in methanol is added to a refluxing solution of potassium carbonate in aqueous methanol. The reaction mixture is refluxed for an additional 3 hours and concentrated under vacuum. The concentrate is poured onto water and the solid which forms is removed by filtration. Crystallization of this solid from an ether solution yields 3β-(2'-tetrahydropyranyloxy)-17β-trimethylsiloxy-5-androsten-19-ol.

Substituting 3-t-butyldimethylsiloxy-17β-trimethylsiloxy-5-androsten-19-ol acetate and 3β-(4'-tetrahydropyranyloxy)-17β-trimethylsiloxy-5-androsten-19-ol acetate for the 3β-(2'-tetrahydropyranyloxy)-17β-trimethylsiloxy-5-androsten-19-ol acetate above results in the formation of 3-t-butyldimethylsiloxy-17β-trimethylsiloxy-5-androsten-19-ol and 3β-(4'-tetrahydropyranyloxy)-17β-trimethylsiloxy-5-androsten-19-ol, respectively.

EXAMPLE 86

3β-(2'-Tetrahydropyranyloxy)-17β-trimethylsiloxy-5-androsten-19-one

One equivalent of Jones Reagent is added to a solution of 3β-(2'-tetrahydropyranyloxy)-17β-trimethylsiloxy-5-androsten-19-ol in acetone at 10° C. After stirring for 15 minutes the acetone layer is poured into cold water with vigorous stirring. The solid which forms is filtered, washed with water and dried in a vacuum oven. Crystallization of this solid from a solution of hexane yields the desired 3β-(2'-tetrahydropyranyloxy)-17β-trimethylsiloxy-5-androsten-19-one.

Substituting 3-t-butyldimethylsiloxy-17β-trimethylsiloxy-5-androsten-19-ol and 3β-(4'-tetrahydropyranyloxy)-17β-trimethylsiloxy-5-androsten-19-ol for the 3β-(2'-tetrahydropyranyloxy)-17β-trimethylsiloxy-5-androsten-19-ol above results in the preparation of 3-t-butyldimethylsiloxy-17β-trimethylsiloxy-5-androsten-19-one and 3β-(4'-tetrahydropyranyloxy)-17β-trimethylsiloxy-5-androsten-19-one, respectively.

EXAMPLE 87

3β-Ethoxy-5-androstene-17β,19-diol diacetate

5-Androstene-3β,17β,19-triol 17,19-diacetate is dissolved in methylenechloride and triethyloxonium fluoroborate added thereto. After stirring for a period of about two hours at room temperature, water is added to the reaction mixture. The methylenechloride layer is dried over magnesium sulfate and concentrated to dryness. The residue is crystallized from an acetone-hexane mixture to yield the desired 3β-ethoxy-5-androstene-17β,19-diol diacetate.

EXAMPLE 88

3β-Ethoxy-5-androstene-17β,19-diol 17-acetate

3β-Ethoxy-5-androstene-17β,19-diol diacetate is added to an aqueous methanol solution of potassium carbonate and the reaction solution stirred at room temperature for about 2 hours. The reaction mixture is poured onto water, and the oil which results is extracted into ether. The ether extract is washed with water, dried over magnesium sulfate and concentrated to dryness. Crystallization of the residue from an ether-pentane mixture yields 3β-ethoxy-5-androstene-17β,19-diol 17-acetate.

Substituting 3β-trimethylsiloxy-5-androstene-17β,19-diol diacetate, 3β-(1'-methoxycyclopentyloxy)-5-androstene-17β,19-diol diacetate and 3β-(1'-cyclopentenyloxy)-5-androstene-17β,19-diol diacetate for the 3β-ethoxy-5-androstene-17β,19-diol diacetate above results in the preparation of 3β-trimethylsiloxy-5-androstene-17β,19-diol 19-acetate, 3β-(1'-methoxycyclopentyloxy)-5-androstene-17β,19-diol 17-acetate and 3β-(1'-cyclopentenyloxy)-5-androstene-17β,19-diol 17-acetate, respectively.

EXAMPLE 89

3β-Ethoxy-17β-hydroxy-5-androsten-19-one acetate

One equivalent of Jones Reagent is added to a solution of 3β-ethoxy-5-androstene-17β,19-diol 17-acetate in acetone at 10° C. After stirring for 30 minutes the acetone layer is poured onto cold water with vigorous stirring. The precipitate which forms is filtered, washed with water and dir dried. Crystallization of this precipitate from an ether-hexane mixture yields 3β-ethoxy-17β-hydroxy-5-androsten-19-one acetate.

Substituting 3β-trimethylsiloxy-5-androstene-17β,19-diol 17-acetate, 3β-(1'-methoxycyclopentyloxy)-5-androstene-17β,19-diol 17-acetate and 3β-(1'-cyclopentenyloxy)-5-androstene-17β,19-diol 17-acetate for the 3β-ethoxy-5-androstene-17β,19-diol 17-acetate above results in the preparation of 17β-hydroxy-3β-trimethylsiloxy-5-androsten-19-one acetate, 17β-hydroxy-3β-(1'-methoxycyclopentyloxy)-5-androsten-19-one acetate and 3β-(1'-cyclopentenyloxy)-17β-hydroxy-5-androsten-19-one acetate, respectively.

EXAMPLE 90

3β-Ethoxy-17β-hydroxy-5-androsten-19-one

A solution of 3β-ethoxy-17β-hydroxy-5-androsten-19-one acetate and sodium carbonate in 10% aqueous methanol is refluxed for a period of about four hours. The cooled solution is poured onto water. The crystals which form are filtered and recrystallized from an acetone-water mixture to yield 3β-ethoxy-17β-hydroxy-5-androsten-19-one.

Substituting 17β-hydroxy-3β-trimethylsiloxy-5-androsten-9-one acetate, 17β-hydroxy-3β-(1'-methoxycyclopentyloxy)-5-androsten-19-one acetate and 3β-(1'-cyclopentenyloxy)-17β-hydroxy-5-androsten-19-one acetate for the 3β-ethoxy-17β-hydroxy-5-androsten-19-one acetate above results in the preparation of 17β-hydroxy-3β-trimethylsiloxy-5-androsten-19-one, 17β-hydroxy-3β-(1'-methoxycyclopentyloxy)-5-androsten-19-one and 3β-(1'-cyclopentenyloxy)-17β-hydroxy-5-androsten-19-one, respectively.

EXAMPLE 91

The following Example is illustrative of the behavioral activity for the compounds of this invention.

Copulatory behavioral tests are conducted in mature, sexually experienced Sprague-Dawley male rats that were either intact or castrated-adrenalectomized. Castration and adrenalectomy reduces the effect on behavior associated with endogenous steroids and/or their metabolites. The onset and intensity of behavioral responses related to mounting, intromission and ejaculation are determined both prior to and after an interval of at least two weeks post-surgery. Five animals per group are subcutaneously administered 500 micrograms/kg of 3β,19-dihydroxy-androst-5-en-17-one 3-acetate, testosterone or 0.25 ml/kg of olive oil vehicle for a period of 14 days. Ten minute behavioral observations are made in the presence of a receptive female rat on days 2, 8, 12 and 15 of the treatment period.

As shown in the table below at least two weeks after castration and adrenalectomy both the intromission frequency and the percent of animals responding is very low in comparison to their former intact state. Following testosterone treatment the castrated-adrenalectomized rats generally approach their pre-surgical sexual pattern of behavior after about 12 days of treatment. Castrated-adrenalectomized rats treated with 3β,19-dihydroxy-androst-5-en-17-one 3-acetate also approach their presurgical sexual pattern of behavior after about day 12 of treatment. More importantly, however, the somatic androgenic effect upon the sex accessory organs of immature castrated rats receiving 3β,19-dihydroxy-androst-5-en-17-one 3-acetate is considerably less than with similar animals receiving testosterone treatment.

| | MEAN NUMBER OF INTROMISSIONS AND PERCENT OF RATS DISPLAYING INTROMISSION PER 10 MINUTE OBSERVATION PERIOD | | | | | | | | | | | |
|---|---|---|---|---|---|---|---|---|---|---|---|---|
| | Pre-Treatment | | | | Treatment Period (14 days) | | | | | | | |
| | Pre Surgery | | Post Surgery | | 2nd Day | | 8th Day | | 12th Day | | 15th Day | |
| Treatment | No. | % | No. | % | No. | % | No. | % | No. | % | No. | % |
| ADRENALECTOMIZED - CASTRATED | | | | | | | | | | | | |
| Vehicle (Olive Oil) | 15.6 | 100 | 2.4 | 20 | 3.4 | 20 | 0.0 | 0 | *NT | | 4.0 | 20 |
| Testosterone 500 μg/kg s.c. | 17.2 | 100 | 0.6 | 40 | 2.8 | 80 | 11.4 | 100 | *NT | | 19.8 | 100 |
| 3β,19-dihydroxy-androst-5-en-17-one 3-acetate 500 μg/kg s.c. | 14.0 | 100 | 0.0 | 0 | *NT | | *NT | | 7.3 | 75 | *NT | |
| INTACT | | | | | | | | | | | | |
| Vehicle (Olive Oil) | 12.6 | 100 | 16.2 | 80 | 19.0 | 100 | 20.8 | 100 | *NT | | 19.6 | 100 |

*NT = Not Tested

EXAMPLE 92

Preparation of a tablet formulation

One thousand tablets for oral use, each containing 25 mg of 3β,17β-di(2'-tetrahydropyranyloxy)androst-5-en-19-ol are prepared according to the following formulation:

| | Gm |
|---|---|
| (a) 3β, 17β-di(2'-tetrahydropyranyloxy)-androst-5-en-19-ol | 25 |
| (b) Dicalcium phosphate | 150 |
| (c) Methylcellulose, U.S.P. (15 cps) | 6.5 |
| (d) Talc | 20 |
| (e) Calcium stearate | 2.5 |

The 3β,17β-di(2'-tetrahydropyranyloxy)androst-5-en-19-ol and dicalcium phosphate are mixed well, granulated with a 7.5% aqueous solution of methylcellulose, passed through a No. 8 screen and carefully dried. The dried granules are passed through a No. 12 screen, blended with talc and calcium stearate and compressed into tablets.

EXAMPLE 93

Preparation of a capsule formulation

One thousand two-piece hard gelatin capsules for oral use each containing 10 mg of 3β-(1'-cyclohexenyloxy)-androst-5-ene,17,19-dione are prepared from the following ingredients:

| | Gm |
|---|---|
| (a) 3β-(1'-Cyclohexenyloxy)androst-5-ene-17,19-dione | 10 |
| (b) Lactose, U.S.P. | 100 |
| (c) Starch, U.S.P. | 10 |
| (d) Talc, U.S.P. | 5 |
| (e) Calcium stearate | 1 |

The finely powdered materials are mixed until uniformly dispersed and filled into hard shelled gelatin capsules of the appropriate size.

In a similar fashion one-piece soft gelatin capsules can be prepared in which the above formulation can be granulated, slugged or compressed directly into a rotary die or plate mold in which the capsule is formed. Alternatively, the above excipients may be omitted and the active ingredient dispensed as a powder directly into the capsule.

EXAMPLE 94

Preparation of an intramuscular injection

A sterile aqueous suspension suitable for intramuscular injection is prepared from the following ingredients:

| | Gm |
|---|---|
| (a) 3β-Hydroxy-7α-methyl-androst-5-ene-17,19-dione 3-propionate | 1 |
| (b) Polyethylene glycol 4000, U.S.P. | 3 |
| (c) Sodium chloride | 0.9 |
| (d) Polyoxyethylene derivatives of sorbitan monooleate (TWEEN 80) U.S.P. | 0.4 |
| (e) Sodium metabisulfite | 0.1 |
| (f) Methylparaben, U.S.P. | 0.18 |
| (g) Propylparaben, U.S.P. | 0.02 |
| (h) Water for injection q.s. to 100 ml | |

The parabens, sodium metabisulfite and sodium chloride are dissolved in approximately one-half the volume of water for injection at 80° C. with stirring. The solution is cooled to below 40° C. and the active ingredient is dissolved therein followed by the polyethylene glycol 4,000 and polyoxyethylene derivatives of sorbitan monooleate. The cooled solution is adjusted to the final volume with water for injection and is then sterilized by sterile filtration through a suitable filter. Each one ml of solution contains 10 mg of 3β-hydroxy-7α-methyl-androst-5-ene-17,19-dione 3-propionate as the active ingredient.

We claim:

1. A method of enhancing the libido of mammals in need thereof which comprises the administration to such mammals of a libido enchancing effective amount of a 19-oxygenated-androst-5-ene having the formula

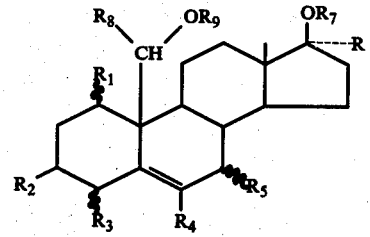

wherein
$R_1$, $R_3$, $R_4$ and $R_5$ are hydrogen and methyl,
$R_2$ is selected from the group consisting of $H_2$, oxo and $H(OR_{10})$,
$R_6$ is selected from the group consisting of hydrogen, lower alkyl having from 1 to 6 carbon atoms, lower alkenyl having from 2 to 6 carbon atoms, lower alkynyl having from 2 to 6 carbon atoms and when taken together with $OR_7$ is oxo,
$R_7$, $R_9$ and $R_{10}$ are each selected from the group consisting of hydrogen, acyl having from 1 to 12 carbon atoms, an ether radical selected from the group consisting of lower alkyl having from 1 to 3 carbon atoms, trialkylsilyl in which the alkyl group has from 1 to 5 carbon atoms, triphenylsilyl, 2-tetrahydropyranyl, 4-tetrahydropyranyl, 1-cycloalkenyl having from 5 to 7 carbon atoms, 1-methoxycycloalkyl and 1-ethoxycycloalkyl in which the cycloalkyl group has from 5 to 7 carbon atoms, and
$R_8$ is hydrogen and when taken together with $OR_8$ is oxo.

2. A method according to claim 1 in which the mammals are primates.

3. A method of counteracting depression associated with a diminished libido for primates in need thereof which comprises the administration to such primates of an anti-depression effective amount of a 19-oxygenated-androst-5-ene of claim 1.

4. A method according to claim 1 in which the 19-oxygenated-androst-5-ene is administered in a total daily dose of from 0.1 milligram to 3 grams.

* * * * *

UNITED STATES PATENT AND TRADEMARK OFFICE
CERTIFICATE OF CORRECTION

PATENT NO. : 4,139,617

DATED : February 13, 1979

INVENTOR(S) : Joyce F. Grunwell and Vladimir Petrow

It is certified that error appears in the above-identified patent and that said Letters Patent are hereby corrected as shown below:

Column 3, line 18, "1butenyl" should read "1-butenyl".
Column 16, line 67, "5androstene" should read "5-androstene".
Column 24, line 13, "dihydoxy" should read "dihydroxy".
Column 25, line 4, "choranil" should read "chloranil".
Column 28, line 52, "19-hyroxy" should read "19-hydroxy".
Column 40, line 13, "19Hydroxy" should read "19-Hydroxy".
Column 40, line 67, "-19;1-hydroxy" should read "-19-hydroxy".
Column 41, line 14, "layeris" should read "layer is".
Column 43, line 27, "dir" should read "air".

UNITED STATES PATENT AND TRADEMARK OFFICE
CERTIFICATE OF CORRECTION

PATENT NO. : 4,139,617
DATED : February 13, 1979
INVENTOR(S) : Joyce F. Grunwell and Vladimir Petrow It is certified that error appears in the above-identified patent and that said Letters Patent are hereby corrected as shown below:

Column 46, lines 25-35, Claim 1, In the formula,

"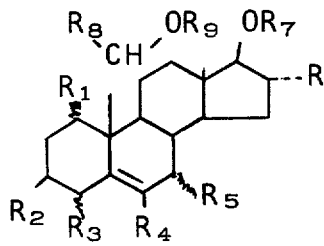"

should read

"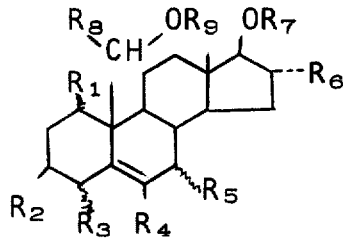"

Signed and Sealed this

First Day of April 1980

[SEAL]

Attest:

SIDNEY A. DIAMOND

Attesting Officer     Commissioner of Patents and Trademarks